(12) United States Patent
Ting et al.

(10) Patent No.: US 11,918,621 B2
(45) Date of Patent: Mar. 5, 2024

(54) METHODS AND TREATMENTS USING TOLL-LIKE RECEPTOR AGONISTS TO MITIGATE HEMATOPOIETIC MYELOID LOSS, INCREASE GASTROINTESTINAL RECOVERY AND REDUCE TUMOR GROWTH

(71) Applicant: The University of North Carolina at Chapel Hill, Chapel Hill, NC (US)

(72) Inventors: Jenny P.-Y. Ting, Chapel Hill, NC (US); Willie June Brickey, Durham, NC (US); Hao Guo, Hillsborough, NC (US); Cathryn Julia Robbins, Redwood City, CA (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 657 days.

(21) Appl. No.: 16/761,063

(22) PCT Filed: Nov. 19, 2018

(86) PCT No.: PCT/US2018/061720
§ 371 (c)(1),
(2) Date: May 1, 2020

(87) PCT Pub. No.: WO2019/099967
PCT Pub. Date: May 23, 2019

(65) Prior Publication Data
US 2020/0282006 A1    Sep. 10, 2020

Related U.S. Application Data

(60) Provisional application No. 62/587,646, filed on Nov. 17, 2017.

(51) Int. Cl.
*A61K 38/08* (2019.01)
*A61K 9/00* (2006.01)
*A61P 35/00* (2006.01)

(52) U.S. Cl.
CPC ............ *A61K 38/08* (2013.01); *A61K 9/0019* (2013.01); *A61K 9/0053* (2013.01); *A61P 35/00* (2018.01)

(58) Field of Classification Search
CPC ........... C07K 14/30; C07K 7/06; A61K 38/08
See application file for complete search history.

(56) References Cited

U.S. PATENT DOCUMENTS

| | | |
|---|---|---|
| 2013/0280264 A1 | 10/2013 | Davila |
| 2015/0065414 A1* | 3/2015 | Long ............... C07K 14/31 514/2.7 |
| 2016/0331810 A1 | 11/2016 | Slingluff, Jr. |

FOREIGN PATENT DOCUMENTS

| | | | |
|---|---|---|---|
| WO | WO-2006091591 A1 * | 8/2006 | ......... A61K 31/4745 |
| WO | 2018053508 A1 | 3/2018 | |

OTHER PUBLICATIONS

Kurkjian et al., "The Toll-Like Receptor 2/6 Agonist, FSL-1 Lipopeptide, Therapeutically Mitigates Acute Radiation Syndrome", Scientific Reports, 2017, 1-13 (Year: 2017).*
Schneider et al. "Tumour suppression induced by the macrophage activating lipopeptide MALP-2 in an ultrasound guided pancreatic carcinoma mouse model", Gut, 2004, 355-361 (Year: 2004).*
Okusawa et al., "Relationship between Structures and Biological Activities of Mycoplasmal Diacylated Lipopeptides and Their Recognition by Toll-Like Receptors 2 and 6". Infection and Immunity, 2004, 1657-1665 (Year: 2004).*
Kole et al., "Type I IFNs Regulate Effector and Regulatory T Cell Accumulation and Anti-Inflammatory Cytokine Production during T Cell-Mediated Colitis", The Journal of Immunology, 2013, 2271-2279 (Year: 2013).*
R. Van Os et al "Granulocyte colony-stimulating factor ehances bone marrow stem cell damage cause by repeated administration of cytotoxic agents," Blood, Sep. 15, 1998.
Shibata, Ken-ichiro et al, "The N-Terminal Lipopeptide of a 44-kDa Membrane-Bound Lipoprotein of Mycoplasma salivarium is Responsible for the Expression of Intercellular Adhesion Molecule-1 on the Cell Surface of Normal Human Gingival Fibroblasts," J Immunol, 2000.
H Khoury et al, "Adverse side-effects associated with G-CSF in patients with chronic myeloid leukemia undergoing allogeneic peripheral blood stem cell transplation," Bone Marrow Transplation 2000.
Takeuchi, Osamu et al, "Discrimination of bacterial lipoproteins by Toll-like receptor 6," International Immunology, vol. 13, No. 7, pp. 993-940, 2001.
Okusawa, Tsugumi et al, "Relationship between Structures and Biological Activities of Mycoplasmal Diacylated Lipopeptides and Their Recognition by Toll-Like Receptors 2 and 6," Infection and Immunity, Mar. 2004, pp. 1657-1665.
R.F. Gude et al, "Effects of Niosomal Cisplatin and Combination of the Same with Theophylline and with Activated Macropages in Murine B16F10 Melanoma Model," Cancer Biotherapy & Radiopharmaceuticals, vol. 17, No. 2 Jul. 5, 2004.
Matam Vijay-Kumar et al, "Flagellin Treatment Protects against Chemicals, Bacteria, Viruses and Radiation," The Journal of Immunology, Jun. 15, 2008.

(Continued)

*Primary Examiner* — Lianko G Garyu
(74) *Attorney, Agent, or Firm* — KDW FIRM PLLC

(57) ABSTRACT

Provided herein are methods of mitigating and/or preventing side effects from chemotherapy and/or radiotherapy in a subject by administering a therapeutically effective amount of a toll-like receptor 2/6 (TLR 2/6) ligand, including fibroblast-stimulating lipopeptide 1 (FSL-1). Methods of treating and/or preventing gastrointestinal disorders are also disclosed. Additionally, methods of increasing granulocyte colony-stimulating factor (G-CSF) production in a subject undergoing a medical treatment, including administering FSL-1 compositions, are provided.

5 Claims, 17 Drawing Sheets

(56) References Cited

OTHER PUBLICATIONS

William A Rose II et al, "FSL-1, a bacterial-derived toll-like receptor 2/6 agonist, enhances resistance to experimental HSV-2 Infection," Virol J, Nov. 10, 2009.
Irving C. Allen et al, "The NLRP3 inflammasome functions as a negative regulator of tumorigenesis during colitsis-associated cancer," J Exp Med, May 10, 2010.
Soren M. Johnson et al, "Mitigation of hematologic radiation toxicity in mice through pharmacological quiescence induced by CDK4/6 inhibition," The Journal of Clinical Investigation, 2010.
Belinda Avalos et al, "Can G-CSF Cause Leukemia in Hematopoietic Stem Cell Donors?," American Society for Blood and Marrow Transplantation, 2011.
C. Zhang et al, "Radioprotection of bone marrow hematopoiesis by CpG-oligodeoxynucleotide administered to mice after total-body irradiation," Journal of Radiation Research, 2011.
Vijay K. Singh et al, "CBLB613: A TLR 2/6 Agonist, Natural Lipopeptide of Mycloplasma arginini, as a Novel Radiation Countermeasure," Radiation Research 2011.
Alexander N. Shakhov et al, "Prevention and Mitigation of Acute Radiation Syndrome in Mice by Synthetic Lipopeptide Agonists of Toll-Like Receptor 2 (TLR2)," PLOS ONE, 2012.
C Liu et al, "A critical role of toll-like receptor 4 (TLR4) and its' in vivo ligands in basal radio-resistance," Cell Death and Disease 2013.
Chao Zhang et al, "CpG-Oligodeoxynucleotide Treatment Protects against Ionizing Radiation-Induction Intestine Injury," PLOS One 2013.
Fu Gao et al, "A critical role of toll-like receptor 2 (TLR2) and its' in vivo ligands in radio-resistance," www.nature.com/scientific reports, 2015.
Justin Wilson et al, "Inflammasome-independent role of AIM2 in suppressing colon tumorigenesis via DNA-PK and Akt." Naturemedicine Jun. 24, 2015.
Roy E. Smith et al, "Acute Myeloid Leukemia and Myelodysplastic Syndrome After Doxorubcin-Cyclophoshosphamide Adjuvant Therapy For Operable Breast Cancer: The National Surgical Adjuvant Breast and Bowel Project Experience," Journal of Clinical Oncology, vol. 21, Issue 7, Apr. 1, 2016.
Cathyrn J. Kurkjian et al, "The Toll-Like Receptor 2/6 Agonist, FSL-1 Lipopeptide, Therapeutically Mitigates Acute Radiation Syndrome," www.nature.com/scientificreports, Dec. 11, 2017.
M. H. Freedman, "Myelodysplasia syndrome and acute myeloid leukemia in patients with congenital neutropenia receiving G-CSF therapy," Blood, Jul. 15, 2000.
International Search Report and Written Opinion for Application No. PCT/US2018/061720 dated Feb. 21, 2019.

* cited by examiner

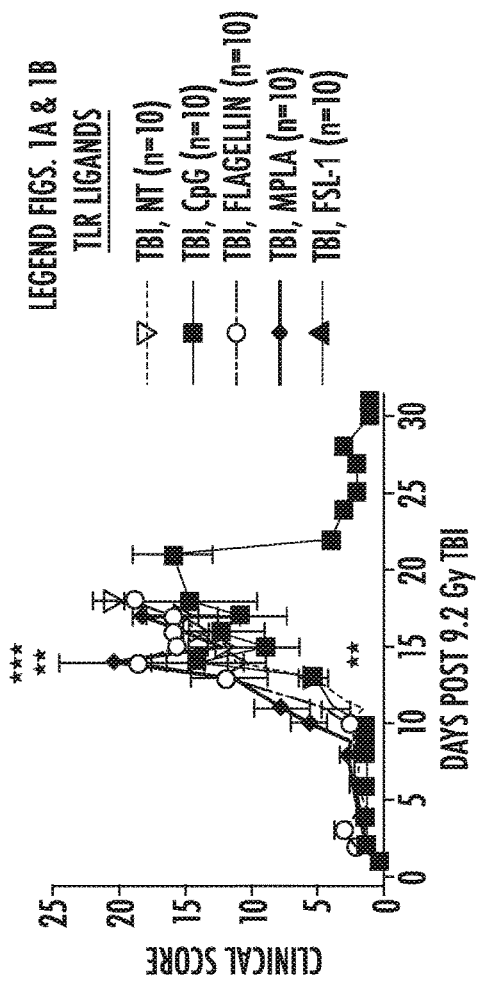
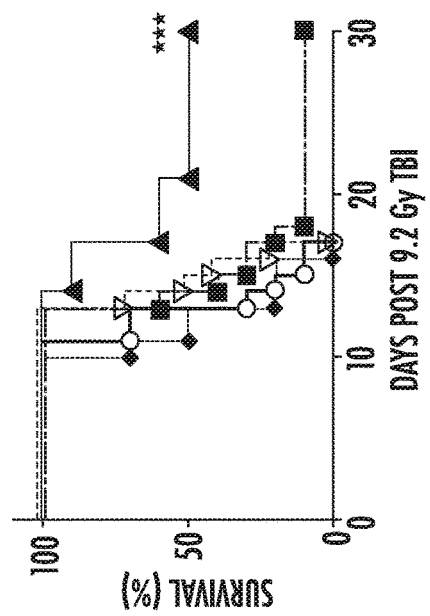
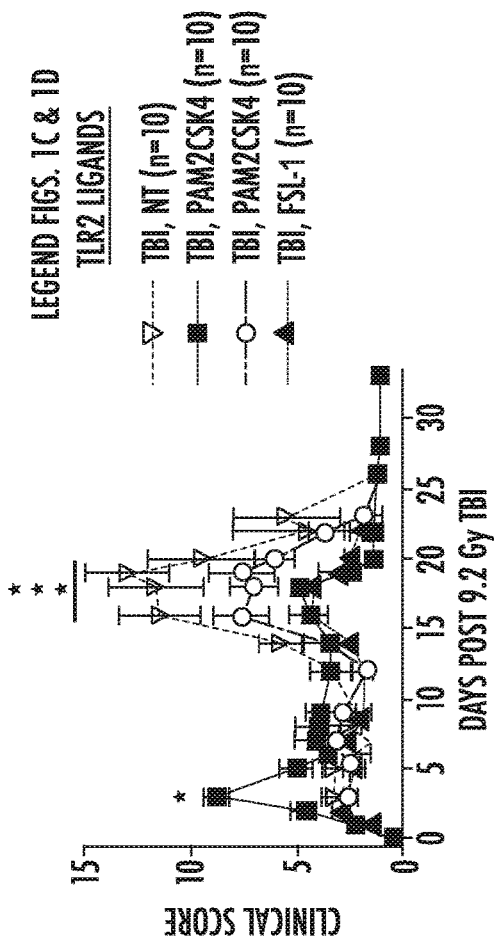
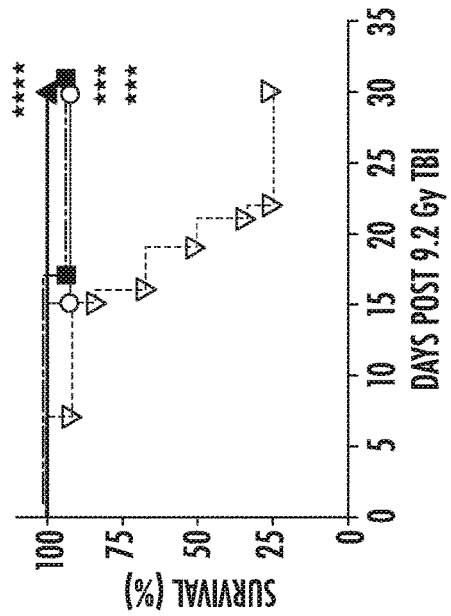

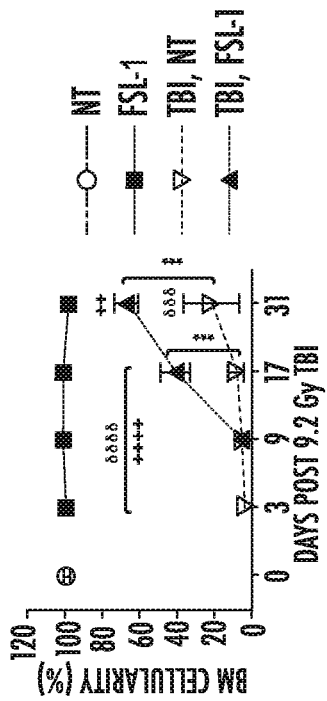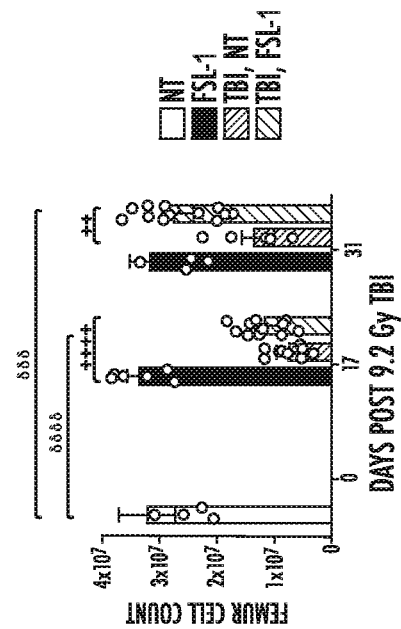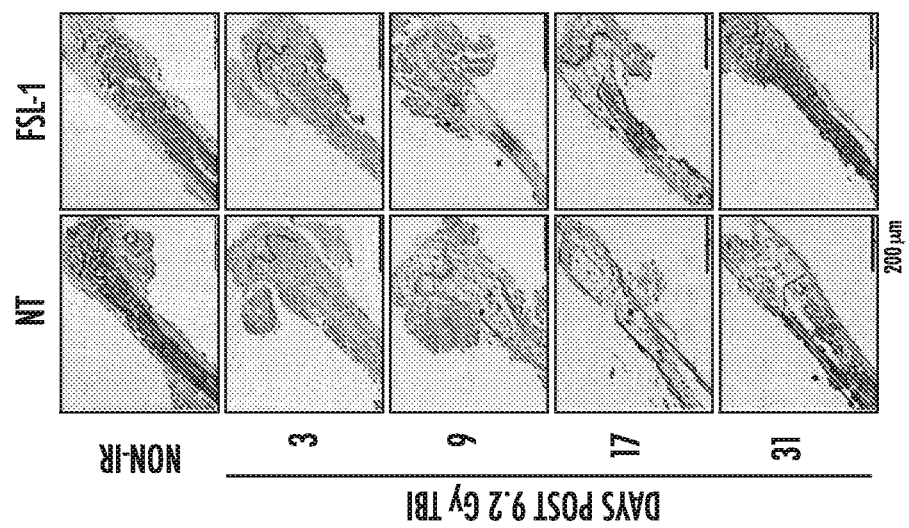

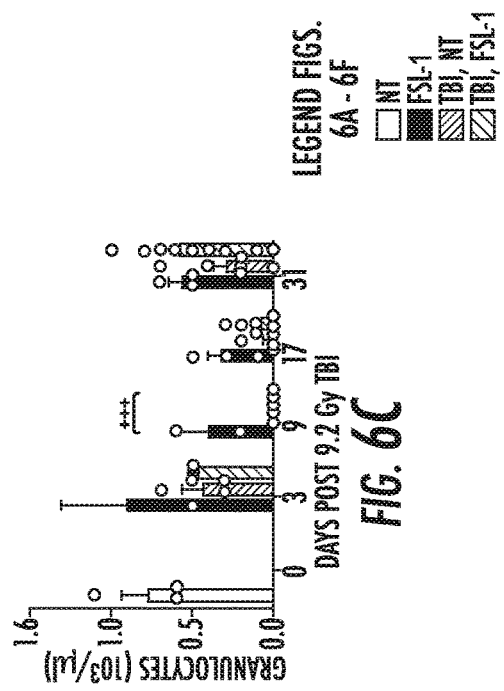
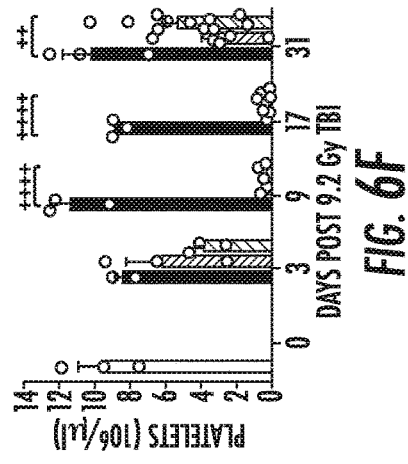
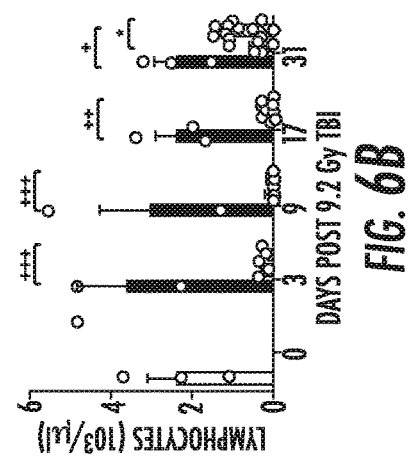
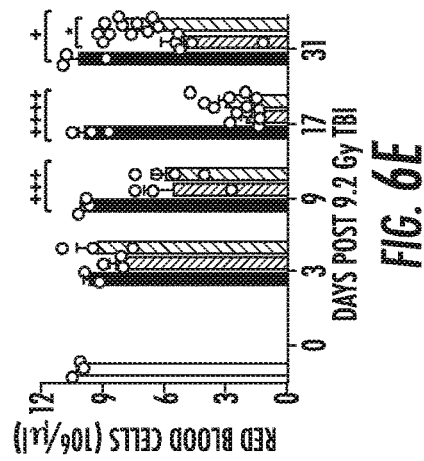
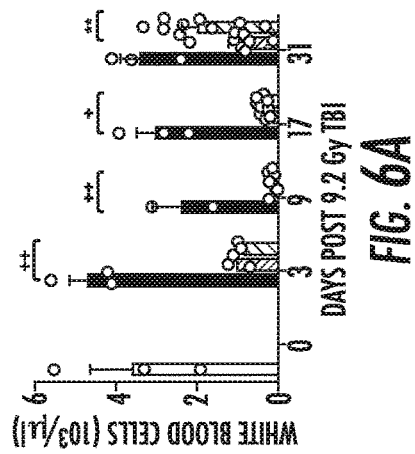
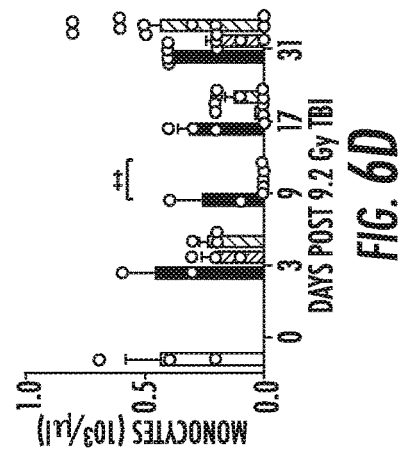

METHODS AND TREATMENTS USING TOLL-LIKE RECEPTOR AGONISTS TO MITIGATE HEMATOPOIETIC MYELOID LOSS, INCREASE GASTROINTESTINAL RECOVERY AND REDUCE TUMOR GROWTH

CROSS-REFERENCE TO RELATED APPLICATIONS

This application claims benefit of U.S. Provisional Patent Application Ser. No. 62/587,646, filed Nov. 17, 2017, herein incorporated by reference in its entirety.

GRANT STATEMENT

This invention was made with government support under U19-AI067798 awarded by the National Institutes of Health. The government has certain rights in the invention.

TECHNICAL FIELD

Disclosed herein in some embodiments are methods and treatments using toll-like receptor agonists to mitigate hematopoietic myeloid loss, increase gastrointestinal recovery and reduce tumor growth. For example, in some embodiments administration of fibroblast-stimulating lipopeptide (FSL-1) mitigates and/or prevents side effects from chemotherapy.

BACKGROUND

Existing cancer treatments and therapeutics, including for example radiation or chemotherapeutic drugs, are often designed to target malignant cells based on their differences in growth control versus normal cells. However, even the most successful cancer treatments often cause side effects, including adversely affecting normal rapidly dividing or apoptosis-prone tissues and cells, e.g. hematopoiesis, small intestine, hair follicles, etc. As a result, there continues to be a need for therapeutic agents to mitigate the side effects associated with chemotherapy and radiation therapy in the treatment of cancer.

Moreover, deliberate or accidental radiation release in the cases of terrorism and nuclear warfare or energy plant and waste facility explosions respectively, can expose a diverse population to various degrees of penetrating ionizing radiation. Acute radiation syndrome (ARS) is a disease state that occurs following partial or whole body exposure to ionizing radiation. ARS can be further characterized into hematopoietic (WARS), gastrointestinal (GI) and cerebrovascular syndromes, which develop based on the type, dose and rate of radiation received. Medical treatments, therefore, targeting hematopoiesis would be vital during a mass casualty event. Replenishment of hematopoietic sites is critical for recovery following radiation exposure. Therefore, medical interventions that can be administered to counteract injury associated with radiation are critically needed.

Similarly, conditions and diseases other than radiation exposure and chemotherapy can cause damage to rapidly dividing cells and tissues that requires medical intervention. For example, inflammatory colitis can significantly impact the health of gastrointestinal epithelial tissues and cells. As a result, there continues to be a need for therapeutic agents and approaches to treat such conditions.

This instant disclosure addresses these needs and provides other related advantages.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this summary does not list or suggest all possible combinations of such features.

In some embodiments, provided herein are methods of mitigating and/or preventing side effects from chemotherapy in a subject, the methods comprising providing a subject to be treated with a chemotherapeutic agent, and/or a subject already treated with a chemotherapeutic agent, and administering to the subject a therapeutically effective amount of a toll-like receptor 2/6 (TLR 2/6) ligand, wherein side effects from chemotherapy are substantially mitigated and/or prevented in the subject. The TLR 2/6 ligand can be administered orally, intraperitoneally or subcutaneously. The subject can be a human, optionally wherein the subject is suffering from a cancer, tumor or related condition. The TLR 2/6 ligand can comprise a synthetic diacylated lipoprotein. The synthetic diacylated lipoprotein can comprise fibroblast-stimulating lipopeptide 1 (FSL-1), or derivative thereof.

In some aspects, administration of FSL-1 can attenuate hematopoietic and/or gastrointestinal syndrome caused by the chemotherapy. Administration of FSL-1 can stimulate hematopoietic cell recovery in the subject. Administration of FSL-1 can stimulate production of granulocytic cells in the subject. Administration of FSL-1 can stimulate proliferative responses in bone marrow in the subject. Administration of FSL-1 can stimulate hematopoiesis in a spleen of the subject. Administration of FSL-1 can stimulate hematopoietic cell recovery causing an increase in peripheral blood cell populations. Administration of FSL-1 can increase granulocyte colony-stimulating factor (G-CSF) production in the subject. Administration of FSL-1 can increase hematopoietic stem cell production and myeloid progenitor cell production in bone marrow of the subject. Administration of FSL-1 can increase neutrophil production in peripheral blood in the subject. Administration of FSL-1 can protect against inflammation-induced gastrointestinal epithelia injury in the subject. In some aspects, the subject can also be receiving radiation therapy.

Also provided herein in some embodiments are methods of treating and/or preventing gastrointestinal disorders in a subject, the methods comprising providing a subject suffering from a gastrointestinal disorder and/or susceptible to gastrointestinal injury, and administering to the subject a therapeutic composition comprising a therapeutically effective amount of fibroblast-stimulating lipopeptide 1 (FSL-1) or derivative thereof, wherein administration of the therapeutic composition comprising a therapeutically effective amount of FSL-1 substantially treats and/or prevents gastrointestinal injury. Administration of the therapeutic FSL-1 can enhance gastrointestinal epithelial tissue health. In some aspects, the subject can be suffering from enterocolitis and/or is susceptible to developing enterocolitis. In some aspects, the subject is a human, optionally wherein the subject is suffering from a cancer, tumor or related condition. In some aspects, the subject is undergoing or about to undergo a cancer therapy comprising radiation therapy, chemotherapy and/or a combination thereof. In some aspects, the therapeutic composition comprising a therapeutically effective amount of FSL-1 or derivative thereof is administered orally, intraperitoneally or subcutaneously.

In some embodiments, administration of FSL-1 increases G-CSF production in the subject. Administration of FSL-1 can protect against inflammation-induced gastrointestinal epithelia injury in the subject. In some embodiments, the subject can be suffering from acute radiation syndrome, hematopoietic injury, gastrointestinal injury, cerebrovascular syndrome, cutaneous toxicity, pulmonary toxicity, cardiac toxicity and/or combinations thereof.

Provided herein are methods of increasing granulocyte colony-stimulating factor (G-CSF) production in a subject undergoing a medical treatment, comprising administering to a subject a therapeutic composition comprising a therapeutically effective amount of fibroblast-stimulating lipopeptide 1 (FSL-1) or derivative thereof, wherein G-CSF concentrations in the subject are increased. The FSL-1 can be administered orally, intraperitoneally or subcutaneously. The subject can be a human, optionally wherein the subject is suffering from a cancer, tumor or related condition. The subject can be undergoing or about to undergo a cancer therapy comprising radiation therapy, chemotherapy and/or a combination thereof. Administration of the therapeutic composition comprising a therapeutically effective amount of FSL-1 can stimulate hematopoietic cell recovery, production of granulocytic cells, proliferative responses in bone marrow, hematopoiesis in a spleen, and/or hematopoietic cell recovery causing an increase in peripheral blood cell populations in the subject. The increased G-CSF concentrations can accelerate hematopoietic cell recovery.

Provided herein are methods of treating a tumor and/or a cancer in a subject, comprising providing a subject in need of treatment for a tumor and/or a cancer, administering a chemotherapeutic agent to the subject, and administering to the subject a therapeutic composition comprising a therapeutically effective amount of fibroblast-stimulating lipopeptide 1 (FSL-1) or derivative thereof, wherein the tumor and/or a cancer in the subject is treated, wherein the effectiveness of the treatment of the tumor and/or cancer in the subject is enhanced as compared to a chemotherapeutic agent alone. In some aspects, The FSL-1 or derivative thereof can be administered orally, intraperitoneally or subcutaneously.

Administration of the FSL-1 or derivative thereof can attenuate hematopoietic and/or gastrointestinal syndrome caused by the chemotherapy. Administration of FSL-1 or derivative thereof can stimulate hematopoietic cell recovery in the subject. Administration of FSL-1 or derivative thereof can stimulate production of granulocytic cells in the subject. Administration of FSL-1 or derivative thereof can stimulate proliferative responses in bone marrow in the subject. Administration of FSL-1 or derivative thereof can stimulate hematopoiesis in a spleen of the subject. Administration of FSL-1 or derivative thereof can stimulate hematopoietic cell recovery causing an increase in peripheral blood cell populations. Administration of FSL-1 or derivative thereof can increases G-CSF production in the subject. Administration of FSL-1 or derivative thereof can increase hematopoietic stem cell production and myeloid progenitor cell production in bone marrow of the subject. Administration FSL-1 or derivative thereof can increase neutrophil production in peripheral blood in the subject. Administration of FSL-1 or derivative thereof can protect against inflammation-induced gastrointestinal epithelia injury in the subject.

In any of the methods disclosed herein the subject can also be receiving radiation therapy.

Accordingly, it is an object of the presently disclosed subject matter to provide methods of treatment and therapy as disclosed herein.

This and other objects are achieved in whole or in part by the presently disclosed subject matter. Further, an object of the presently disclosed subject matter having been stated above, other objects and advantages of the presently disclosed subject matter will become apparent to those skilled in the art after a study of the following description, Drawings and Examples.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to an embodiment set forth in the illustrations of the accompanying drawings. Although the illustrated embodiment is merely exemplary of systems for carrying out the presently disclosed subject matter, both the organization and method of operation of the presently disclosed subject matter, in general, together with further objectives and advantages thereof, may be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter.

For a more complete understanding of the presently disclosed subject matter, reference is now made to the following drawings in which:

FIGS. 1A through 1D are graphical depictions of data showing that FSL-1 is effective in promoting survival among TLR ligands upon lethal total body radiation;

FIGS. 2A through 2C are histological staining images and graphical depictions of data showing that FSL-1 stimulates hematopoietic cell recovery post radiation from bone marrow;

FIGS. 6A through 6F are graphical depictions of data showing that FSL-1 stimulates hematopoietic cell recovery post radiation, impacting peripheral blood cell populations;

DETAILED DESCRIPTION

Figure 3A:
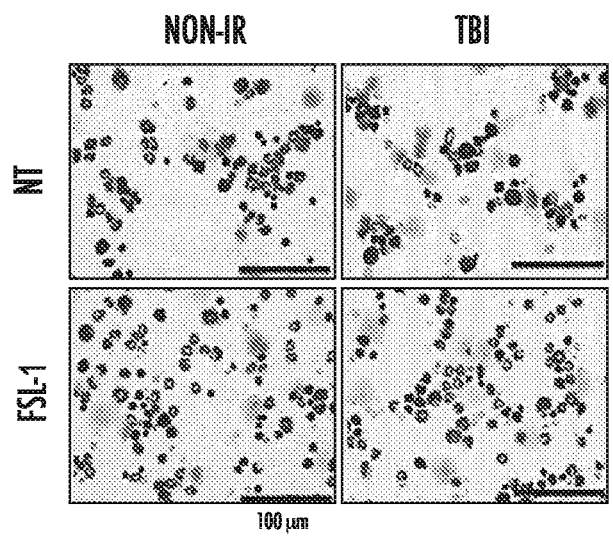
FIGS. 3A and 3B are histological staining images and graphical depictions of data showing granulocytic cells predominate in bone marrow recovery from radiation with FSL-1 treatment.

The presently disclosed subject matter now will be described more fully hereinafter, in which some, but not all embodiments of the presently disclosed subject matter are described. Indeed, the presently disclosed subject matter can be embodied in many different forms and should not be construed as limited to the embodiments set forth herein; rather, these embodiments are provided so that this disclosure will satisfy applicable legal requirements.

Toll-like receptor (TLR) ligands were analyzed for mitigation of side effects of radiation and chemotherapy, and enhancement of therapeutic treatments and cellular recovery. More specifically, TLR 2/6 ligands, including fibroblast-stimulating lipopeptide 1 (FSL-1), were analyzed for their ability to (1) mitigate the side effects of radiation, (2) increase G-CSF and hematopoietic cell recovery, (3) increase blood neutrophils, (4) be administered through an intraperitoneal or subcutaneous route, (5) increase hematopoietic stem cells and common myeloid progenitors, (6) mitigate gastrointestinal colitis and (7) cause a reduction in tumor growth in a tumor model that is difficult to treat. Various TLR ligands were analyzed and compared.

Based on the findings disclosed herein regarding TLR ligands, methods and therapeutic approaches for mitigating the side effects associated with chemotherapy and radiation therapy in the treatment of cancer are provided. Moreover, medical interventions that can be administered to counteract injury associated with radiation are provided. Additionally, treatment approaches and methods for treat conditions causing damage to rapidly dividing cells and tissues are disclosed herein.

Deliberate or accidental radiation release in the cases of terrorism and nuclear warfare or energy plant and waste facility explosions respectively, can expose a diverse population to various degrees of penetrating ionizing radiation. Therefore, medical interventions that can be administered to counteract injury associated with radiation are critically needed. An ideal medical intervention following radiation is defined by the following properties: (1) administration at 24 hours or more post exposure, (2) independent of sex or age, and (3) application to individuals exposed to a variety of radiation doses.

Acute radiation syndrome (ARS) is a disease state that occurs following partial or whole body exposure to ionizing radiation. ARS can be further characterized into hematopoietic (H-ARS), gastrointestinal (GI) and cerebrovascular syndromes, which develop based on the type, dose and rate of radiation received. H-ARS is observed at lower doses of radiation (200-600 rad), but also persists in tandem with GI and cerebrovascular syndromes, which occur only upon exposure to higher doses (600-1,000 rad). Medical treatments, therefore, targeting hematopoiesis would be vital during a mass casualty event.

Replenishment of hematopoietic sites plays a role in recovery following radiation exposure. Regeneration of the hematopoietic system occurs successfully through multiple mechanisms. Hematopoiesis is driven, in part, by various growth factors, including granulocyte colony-stimulating factor (G-CSF), erythropoietin (EPO) and thrombopoietin (TPO). These factors are thought to drive proliferation of granulocytes, erythroid cells, and megakaryocytes, respectively, though some degree of cross-regulation may occur between lineages. Beyond driving granulocyte proliferation, G-CSF can also impact the function of lymphoid lineages. In addition to growth factors, and as disclosed herein, TLR receptors found on progenitor cells can utilize MyD88-dependent mechanisms to drive cellular repopulation following insults to the hematopoietic system.

Furthermore, regulation of hematopoiesis can be driven by upregulating growth factors through TLR signaling, including via FSL-1, as shown herein. In some aspects, such an effect can be based on a correlation between G-CSF and TLR2-dependent signaling. Such can also impact or inhibit apoptosis within the GI tract. Notably, FSL-1 mediated TLR-based impacts, including radioprotective roles and mechanisms, are shown herein for the first time for post-radiation exposure.

In some embodiments, disclosed herein are the mechanisms underlying FSL-1 mediated effects, including radiomitigation. The data herein show that FSL-1, a different class of TLR ligand that can activate TLR2/6, has a role in improving hematopoietic responses associated with radiation, chemotherapy and other events/conditions. The TLR2/6 ligand FSL-1 is identified herein as a potent radiomitigator that is unexpectedly superior to all other TLR ligands.

In some aspects, the data herein demonstrate that a single administration of FSL-1 can positively impact hematopoiesis and induce G-CSF production in a subject. Overall, these data reveal that the immune stimulatory effects of FSL-1 can be used to mitigate radiation injury, chemotherapeutic side effects and other cellular and tissue injury by accelerating hematopoietic recovery at multiple sites.

In some aspects, provided herein are compositions, therapeutics, methods and treatments based on lipopeptides. For example, fibroblast-stimulating lipopeptide FSL-1 (Pam2CGDPKHPKSF), contains a diacylglycerol structure similar to Pam2CSK4, and has roles in immune cell maturation, Th2 immunity and protection from infections. FSL-1 is a synthetic lipopeptide derived from *Mycoplasma salivarium*. The mycoplasmal lipopeptide FSL-1 can contain a diacylated cysteine residue and is recognized by the TLR2/TLR6 heterodimer. In some aspects, FSL-1 can be based on the N-terminal part of the 44-kDa lipoprotein LP44 of *Mycoplasma salivarium*. Further details of the chemical structure and nature of FSL-1 can be found in Shibata, et al., 2000; Okusawa et al., 2004; and Takeuchi O. et al., 2001, each of which is incorporated herein by reference. As disclosed herein, the administration of FSL-1 can mitigate radiation injury, reduce chemotherapeutic side effects and improve other cellular and tissue injury by accelerating hematopoietic recovery at multiple sites.

Generally, lipopeptides are part of the outer membranes of Gram-negative bacteria, Gram-positive bacteria, and mycoplasma. Bacterial lipopeptides have no shared sequence homology, but are characterized by the unusual N-terminal amino acid S-(2,3-dihydroxypropyl)-L-cysteine that is acylated by two or three fatty acids. Synthetic analogues of the N-terminal lipopeptides of natural lipopeptides, including FSL-1, can be potent activators of TLRs and NF-κB, as well as being immunoadjuvants in vivo and in vitro.

Toll-like receptors (TLRs) are a class of proteins that play a role in the innate immune system. They are single, membrane-spanning, non-catalytic receptors usually expressed on sentinel cells such as macrophages and dendritic cells, that recognize structurally conserved molecules derived from microbes.

In some embodiments, TLR agonists and/or ligands used in the disclosed methods of treatment and/or therapy can comprise a truncated or modified ligand/agonist. For example, FSL-1 can in some embodiments be modified or altered to enhance a biologic effect, increase binding to a receptor(s), increase half-life at injection, induce downstream effectors such as G-CSF, increase tissue specificity, and the like.

Methods of Treatment

Disclosed herein are methods of subjects for various conditions based on the TLR ligand data presented herein. Conditions to be treated, directly or as an adjuvant, can include cancer, radiation exposure, gastrointestinal disorders and the like. Subjects to be treated or receive an adjuvant therapy can include those receiving and/or exposed to radiation therapy or chemotherapy; temperature shock; exposure to harmful doses of radiation, e.g., workers in nuclear power plants, the defense industry or radiopharmaceutical production, or soldiers; cell aging; wounding; poisoning; and infection.

Thus, in some embodiments, provided herein are methods of mitigating and/or preventing side effects from chemotherapy in a subject, including for example providing a subject to be treated with a chemotherapeutic agent, and/or a subject already treated with a chemotherapeutic agent, and administering to the subject a therapeutically effective amount of a toll-like receptor 2/6 (TLR 2/6) ligand, wherein side effects from chemotherapy are substantially mitigated and/or prevented in the subject. As disclosed herein, the TLR 2/6 ligand can comprises a synthetic diacylated lipoprotein, including a fibroblast-stimulating lipopeptide 1 (FSL-1), or derivative thereof. The TLR 2/6 ligand can be administered orally, intraperitoneally or subcutaneously.

The subject in such a treatment can be a human, and can be suffering from a cancer, tumor or related condition. In the context of such a method, the administration of FSL-1 can provide a plurality of benefits, including for example, but not limited to, attenuating hematopoietic and/or gastrointestinal syndrome caused by the chemotherapy, radiation or other stress; stimulating hematopoietic cell recovery; stimulating production of granulocytic cells; stimulating proliferative responses in bone marrow; stimulating hematopoiesis in the spleen; stimulating hematopoietic cell recovery causing an increase in peripheral blood cell populations; increasing granulocyte colony-stimulating factor (G-CSF) production; increasing hematopoietic stem cell production and myeloid progenitor cell production in bone marrow; increasing neutrophil production in peripheral blood; and/or protecting against inflammation-induced gastrointestinal epithelia injury.

In the disclosed methods of mitigating and/or preventing side effects from chemotherapy, the administration of the FSL-1 composition can enhance gastrointestinal epithelial tissue health, particularly where the subject is suffering from enterocolitis and/or is susceptible to developing enterocolitis. Such subjects can be undergoing or about to undergo a cancer therapy comprising radiation therapy, chemotherapy and/or a combination thereof. Likewise, such subjects can be suffering from acute radiation syndrome, hematopoietic injury, gastrointestinal injury, cerebrovascular syndrome, cutaneous toxicity, pulmonary toxicity, cardiac toxicity and/or combinations thereof.

Also provided herein are methods of treating and/or preventing gastrointestinal disorders in a subject. By way of example and not limitation, dysfunction of gastrointestinal health can be characterized by changes in epithelial permeability that changes water, nutrients, microbes, proteins, etc.; stool consistency from normal to diarrheal; hydration due to increased permeability of mucosa; microbiome composition due to dysbiosis (disruption of control or balance of microbial communities and loss or overgrowth of bacteria or fungi or other pathogens); and could lead to bleeding, nausea, vomiting, pain, malaise, ulcers, fever, chills and potentially other inflammatory conditions. Thus, methods of treating and/or preventing gastrointestinal disorders can comprise providing a subject suffering from a gastrointestinal disorder and/or susceptible to gastrointestinal injury, and administering to the subject a therapeutic composition comprising a therapeutically effective amount of fibroblast-stimulating lipopeptide 1 (FSL-1) or derivative thereof. Such an administration can substantially treat and/or prevent gastrointestinal injury in the subject, including for example enhancing gastrointestinal epithelial tissue health.

Such a subject can in some embodiments be suffering from enterocolitis and/or be susceptible to developing enterocolitis. Such a subject can in some embodiments be a human, optionally wherein the subject is suffering from a cancer, tumor or related condition. Such a subject can in some embodiments be undergoing or about to undergo a cancer therapy comprising radiation therapy, chemotherapy and/or a combination thereof. The subject can in some embodiments be suffering from acute radiation syndrome, hematopoietic injury, gastrointestinal injury, cerebrovascular syndrome, cutaneous toxicity, pulmonary toxicity, cardiac toxicity and/or combinations thereof.

The therapeutic composition comprising a therapeutically effective amount of FSL-1 or derivative thereof can be administered orally, intraperitoneally or subcutaneously. In some aspects, administration of FSL-1 increases G-CSF production in the subject. In some aspects, administration of FSL-1 protects against inflammation-induced gastrointestinal epithelia injury in the subject.

Also provided herein are methods of increasing granulocyte colony-stimulating factor (G-CSF) production in a subject undergoing a medical treatment, comprising administering to a subject a therapeutic composition comprising a therapeutically effective amount of fibroblast-stimulating lipopeptide 1 (FSL-1) or derivative thereof, wherein G-CSF concentrations in the subject are increased. In such methods the therapeutic composition comprising a therapeutically effective amount of FSL-1 can be administered orally, intraperitoneally or subcutaneously. In some aspects, the subject is a human, optionally wherein the subject is suffering from a cancer, tumor or related condition. In some aspects, the subject is undergoing or about to undergo a cancer therapy comprising radiation therapy, chemotherapy and/or a combination thereof.

In some aspects, administration of the therapeutic composition comprising a therapeutically effective amount of FSL-1 stimulates hematopoietic cell recovery, production of granulocytic cells, proliferative responses in bone marrow, hematopoiesis in a spleen, and/or hematopoietic cell recovery causing an increase in peripheral blood cell populations in the subject. In some embodiments, the increased G-CSF concentrations accelerate hematopoietic cell recovery.

In some embodiments, administration of FSL-1 can be a replacement for current G-CSF therapy or treatments where G-CSF is administered directly. Currently, only one promising radiation countermeasure has been approved by the FDA as an effective countermeasure for ARS. However, G-CSF has been shown to increase the survival of irradiated mice only when injected subcutaneously daily from day 1 to 16 (16 doses), which makes it quite costly and inconvenient to use and limits its application in clinic. What's more, side effects are also a big concern. G-CSF administration may cause fever, myalgia, respiratory distress, hypoxia, splenomegaly, sickle cell crisis and incidences of Sweet's syndrome (acute febrile neutropenia dermatosis/skin plaques). Moreover, there are several lines of evidence show that cancer patients who received G-CSF treatment had an increased risk of developing myelodysplasia (MDS) and acute myeloid leukemia (AML).

Furthermore, G-CSF used in cancer patients may cause myelodysplasia and acute myeloid leukemia (Avalos et al., 2011; Smith et al., 2003; Khoury et al., 2000; Freedman et al., 2000), while the data herein shows that FSL-1 could protect mice from lethal dose TBI and surviving mice could live for more than 600 days without any symptoms of leukemia or other diseases. Additionally, when used as a countermeasure against radiation, Shakhov et al., 2012, showed G-CSF needs to be administered from day 1 to day 16 post TBI to get protection, while the data herein illustrates that FSL-1 given in a single dose at 24 h post TBI provides substantial protection and mitigation. This finding is particularly surprising and beneficial since prior authors expressed concern over multiple administrations of G-CSF in clinic (van Os R, et al., 1998).

Thus, contrary to prior studies with G-CSF, FSL-1 therapy, as disclosed herein, is shown to stimulate in vivo G-CSF production with significantly fewer doses, e.g. one, two, three, four, five, less than 10 or less than 20 doses, and without the above-noted side effects. Thus, the TLR 2/6 ligands, including FSL-1, represent appealing and cost-effective alternatives to conventional G-CSF applications.

Provided in some embodiments is a method of treating a tumor and/or a cancer in a subject. This treatment method can comprise providing a subject in need of treatment for a tumor and/or a cancer, administering a chemotherapeutic agent to the subject, and administering to the subject a therapeutic composition comprising a therapeutically effective amount of fibroblast-stimulating lipopeptide 1 (FSL-1) or derivative thereof, wherein the tumor and/or a cancer in the subject is treated, wherein the effectiveness of the treatment of the tumor and/or cancer in the subject is enhanced as compared to a chemotherapeutic agent alone. In some aspects, the FSL-1 is administered orally, intraperitoneally or subcutaneously.

In some aspects, the FSL-1 administered to the subject can provide a plurality of benefits, including but not limited to, attenuating hematopoietic and/or gastrointestinal syndrome caused by the chemotherapy; stimulating hematopoietic cell recovery; stimulating production of granulocytic cells; stimulating proliferative responses in bone marrow; stimulating hematopoiesis in the spleen; stimulating hematopoietic cell recovery causing an increase in peripheral blood cell populations; increasing G-CSF production; increasing hematopoietic stem cell production and myeloid progenitor cell production in bone marrow; and/or increasing neutrophil production in peripheral blood.

In some embodiments, in such a method of treating a tumor and/or a cancer in a subject, the administration of the therapeutic composition comprising a therapeutically effective amount of FSL-1 or derivative thereof protects against inflammation-induced gastrointestinal epithelia injury in the subject. In some aspects, the subject is also receiving radiation therapy.

In any of the above methods, and/or therapeutic approaches disclosed herein, the administration of the TLR 2/6 ligand, or FSL-1, to the subject occurs before, after and/or simultaneously with administration of chemotherapy.

The compositions, therapeutic agents and the like disclosed herein, alone or in the context of one or more methods, may be administered simultaneously or metronomically with other treatments. The term "simultaneous" or "simultaneously" as used herein, means that the agent and other treatment be administered within 48 hours, preferably 24 hours, more preferably 12 hours, yet more preferably 6 hours, and most preferably 3 hours or less, of each other. The term "metronomically" as used herein means the administration of the agent at times different from the other treatment and at a certain frequency relative to repeat administration.

The compositions, therapeutic agents and the like disclosed herein, alone or in the context of one or more methods, can in some embodiments be administered at any point prior to exposure to the stress or condition, including, but not limited to, about 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, or 1 hr prior to exposure. The compositions, therapeutic agents and the like can be administered at any point after exposure to the stress or condition, including, but not limited to, about 1 hr, 2 hr, 3 hr, 4 hr, 6 hr, 8 hr, 10 hr, 12 hr, 14 hr, 16 hr, 18 hr, 20 hr, 22 hr, 24 hr, 26 hr, 28 hr, 30 hr, 32 hr, 34 hr, 36 hr, 38 hr, 40 hr, 42 hr, 44 hr, 46 hr, or 48 hr after exposure.

Chemotherapy

In some embodiments, the methods of treatment disclosed herein can comprise treatment of, among other conditions, a cancer or tumor. The TLR 2/6 ligands, or FSL-1, can be administered in combination with a cancer treatment, such as chemotherapy or radiation therapy. The cancer treatment can in some embodiments comprise administration of a cytotoxic agent or cytostatic agent, i.e. a chemotherapy, or combination thereof. Cytotoxic agents prevent cancer cells from multiplying by: (1) interfering with the cell's ability to replicate DNA and (2) inducing cell death and/or apoptosis in the cancer cells. Cytostatic agents act via modulating, interfering or inhibiting the processes of cellular signal transduction that regulate cell proliferation.

By way of example and not limitation, classes of compounds that can be used as cytotoxic agents include the following: alkylating agents (including, without limitation, nitrogen mustards, ethylenimine derivatives, alkyl sulfonates, nitrosoureas and triazenes): uracil mustard, chlormethine, cyclophosphamide (Cytoxan®), ifosfamide, melphalan, chlorambucil, pipobroman, triethylene-melamine, triethylenethiophosphoramine, busulfan, carmustine, lomustine, streptozocin, dacarbazine, and temozolomide; antimetabolites (including, without limitation, folic acid antagonists, pyrimidine analogs, purine analogs and adenosine deaminase inhibitors): methotrexate, 5-fluorouracil, floxuridine, cytarabine, 6-mercaptopurine, 6-thioguanine, fludarabine phosphate, pentostatine, and gemcitabine; natural products and their derivatives (for example, vinca alkaloids, antitumor antibiotics, enzymes, lymphokines and epipodophyllotoxins): vinblastine, vincristine, vindesine, bleomycin, dactinomycin, daunorubicin, doxorubicin, epirubicin, idarubicin, ara-c, paclitaxel (paclitaxel is commercially available as Taxol®), mithramycin, deoxyco-formycin, mitomycin-c, I-asparaginase, interferons (preferably IFN-α), etoposide, and teniposide. Other proliferative cytotoxic agents include, but are not limited to, navelbene, CPT-11, anastrazole, letrazole, capecitabine, reloxafine, cyclophosphamide, ifosamide, and droloxafine.

Microtubule affecting agents interfere with cellular mitosis and are well known in the art for their cytotoxic activity. Microtubule affecting agents that may be used include, but are not limited to, allocolchicine (NSC 406042), halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, epothilone B, and discodermolide, estramustine, nocodazole, MAP4, and the like.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Cytostatic agents that may be used include, but are not limited to, hormones and steroids (including synthetic analogs): 17 α-ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, hlorotrianisene, hydroxyprogesterone, aminoglutethimide, estramustine, medroxyprogesteroneacetate, leuprolide, flutamide, toremifene, and zoladex.

Other cytostatic agents are antiangiogenics, such as matrix metalloproteinase inhibitors, and other VEGF inhibitors, such as anti-VEGF antibodies and small molecules such as ZD6474 and SU6668 are also included. Anti-Her2 antibodies from Genentech may also be utilized. A suitable EGFR inhibitor is EKB-569 (an irreversible inhibitor). Also included are Imclone antibody C225 immunospecific for the EGFR, and src inhibitors.

Also suitable for use as a cytostatic agent is Casodex® (bicalutamide, Astra Zeneca) which renders androgen-dependent carcinomas non-proliferative. Yet another example of a cytostatic agent is the antiestrogen Tamoxifen® which inhibits the proliferation or growth of estrogen dependent breast cancer. Inhibitors of the transduction of cellular proliferative signals are cytostatic agents. Representative examples include epidermal growth factor inhibitors, Her-2 inhibitors, MEK-1 kinase inhibitors, MAPK kinase inhibitors, PI3 inhibitors, Src kinase inhibitors, and PDGF inhibitors.

In some embodiments, a cancer treatment as disclosed herein can comprise radiation therapy. The radiation therapy can be, for example but not limited to, external beam radiation, internal radiation therapy, or conformal radiation therapy, in which a computer is used to shape the beam of radiation to match the shape of the tumor. The radiation used in radiation therapy can come from a variety of sources, including an x-ray, electron beam, or gamma rays. The doses and timing of administration of the radiation during radiation therapy can and will vary depending on the location and extent of the cancer. The FSL-1 compositions can be administered as a radioprotective agent in combination with the radiation therapy, as described herein.

In some embodiments, cancers that can be treated in the context of the disclosed methods and therapeutic approaches, include, but are not limited to, the following: carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, larynx, pancreas (including exocrine pancreatic carcinoma), mouth, pharynx, esophagus, stomach, small intestine, colon, rectum, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyoscarcoma, and osteosarcoma; and other tumors including melanoma, xenoderma pigmentosum, keratoactanthoma, seminoma, thyroid follicular cancer, and teratocarcinoma.

Radiation Therapy

In some embodiments, the methods of treatment disclosed herein can comprise treatment of, among other conditions, exposure to radiation and subsequent conditions related thereto. The FSL-1 can be administered in combination with a radiation treatment as an adjuvant therapy, or after radiation exposure. Exposure to ionizing radiation (IR) may be short- or long-term, it may be applied as a single dose or multiple doses, to the whole body or locally. Thus, nuclear accidents or military attacks may involve exposure to a single high dose of whole body irradiation. Likewise, single or multiple doses of radiation are frequently used to treat cancers, tumors and the like.

At the molecular and cellullar level, radiation particles may lead to breakage in the DNA and cross-linking between DNA, proteins, cell membranes and other macromolecular structures. Ionizing radiation may also induce secondary damage to the cellular components by giving rise to free radicals and reactive oxygen species (ROS). Multiple repair systems counteract this damage, such as several DNA repair pathways that restore the integrity and fidelity of the DNA, and antioxidant chemicals and enzymes that scavenge the free radicals and ROS and reduce the oxidized proteins and lipids. Cellular checkpoint systems are present to detect the DNA defects and delay cell cycle progression until the damage is repaired or a decision to commit the cell to growth arrest or programmed cell death (apoptosis) is reached.

At the organism level, the immediate effects of low and moderate levels of radiation are largely caused by cell death, which leads to radiation-induced inflammation. At higher radiation levels, the so-called hematopoietic and gastrointestinal syndromes lead to short-term radiation-induced death. The hematopoietic syndrome is characterized by the loss of hematopoietic cells and their progenitors, thereby making it impossible to regenerate blood and the lymphoid system. Death usually occurs as a consequence of infection (due to immunosuppression), hemorrhage and/or anemia. The gastrointestinal syndrome is characterized by massive cell death in the intestinal epithelium, predominantly in the small intestine, followed by the disintegration of the intestinal wall and death from bacteremia and sepsis. The hematopoietic syndrome manifests itself at lower doses of radiation and leads to a more delayed death than the gastrointestinal syndrome. Very high doses of radiation can cause nearly instant death by eliciting neuronal degeneration.

Organisms that survive a period of acute toxicity of radiation may suffer long-term consequences that include radiation-induced carcinogenesis and fibrosis that develop in exposed organs (e.g., kidney, liver or lungs) months and even years after irradiation. Other long-term consequences include immune suppression, and multi-organ system inflammatory diseases including carditis, neuro/cognitive disorders, diabetes, chronic gastrointestinal inflammation.

Administration

In some embodiments, compositions provided herein can be administered orally or subcutaneously. Additionally in some embodiments, administration routes can include any suitable manner including, but not limited to, parenterally, sublingually, transdermally, rectally, transmucosally, topically, via inhalation, via buccal administration, or combinations thereof. Parenteral administration includes, but is not limited to, intravenous, intraarterial, intraperitoneal, subcutaneous, intramuscular, intrathecal, and intratumoral.

Formulations

Compositions provided herein, including those comprising TLR ligands such as FSL-1, can be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch, polyvinylpyrrolidone and biodegradable, polymers such as dextran. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Compositions provided herein, including those comprising TLR ligands such as FSL-1, may also be liquid formulations including, but not limited to, aqueous or oily suspensions, solutions, emulsions, syrups, and elixirs. The compositions may also be formulated as a dry product for constitution with water or other suitable vehicle before use. Such liquid preparations may contain additives including, but not limited to, suspending agents, emulsifying agents, nonaqueous vehicles and preservatives. Suspending agents include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid.

In some embodiments, compositions provided herein, including those comprising TLR ligands such as FSL-1, may also be formulated as suppositories, which may contain suppository bases including, but not limited to, cocoa butter or glycerides. Compositions provided herein may also be formulated for inhalation, which may be in a form including, but not limited to, a solution, suspension, or emulsion that may be administered as a dry powder or in the form of an aerosol using a propellant, such as dichlorodifluoromethane car trichlorofluoromethane. Compositions provided herein may also be formulated as transdermal formulations comprising aqueous or nonaqueous vehicles including, but not limited to, creams, ointments, lotions, pastes, medicated plaster, patch, or membrane.

In some embodiments, compositions provided herein, including those comprising TLR ligands such as FSL-1, may also be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

In some embodiments, compositions provided herein, including those comprising TLR ligands such as FSL-1, may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Dosage

A therapeutically effective amount of an agent, including TLR ligands and FSL-1, required for use in the disclosed methods and therapies varies with the nature of the condition being treated, the length of time that activity is desired, and the age and the condition of the patient, and is ultimately determined by the attendant physician. In general, however, doses employed for adult human treatment typically are in the range of 0.001 mg/kg to about 1,000 mg/kg per day. The dose may be about 1 µg/kg to about 1000 µg/kg per day. In some embodiments, Food and Drug Administration (FDA) recommendations for dosing can be used, which can be based on the determination of the no observed adverse effect levels (NOAELs) in the tested animal species, the conversion of NOAELs to human equivalency dose (HED) to generate an initial dosing strategy to apply to safety assessment. The calculation is described as: HED=animal dose in mg/kg×(animal weight in kg/human weight in kg)^0.33 (FDA White Paper; 2005; Nair and Jacob, 2016).

The desired dose may be conveniently administered in a single dose, or as multiple doses administered at appropriate intervals, for example as two, three, four or more sub-doses per day. As the data herein suggest, in some embodiments a single dose of FSL-1 can be sufficient.

By way of example and not limitation, the dosage of a TLR 2/6 ligand, including FSL-1 or derivative thereof, or any other inducer of G-CSF, can be any dosage including, but not limited to, about 1 µg/kg, 25 µg/kg, 50 µg/kg, 75 µg/kg, 100 µg/kg, 125 µg/kg, 150 m/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg or 1 mg/kg.

Definitions

The terminology used herein is for the purpose of describing particular embodiments only and is not intended to be limiting of the presently disclosed subject matter.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one skilled in the art. While the following terms are believed to be well understood by one of ordinary skill in the art, the following definitions are set forth to facilitate explanation of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Following long-standing patent law convention, the terms "a", "an", and "the" refer to "one or more" when used in this application, including the claims. Thus, for example, reference to "a unit cell" includes a plurality of such unit cells, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about" when referring to a value or to an amount of a composition, mass, weight, temperature, time, volume, concentration, percentage, etc., is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

The term "comprising", which is synonymous with "including", "containing", or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

EXAMPLES

The following examples are included to further illustrate various embodiments of the presently disclosed subject matter. However, those of ordinary skill in the art should, in light of the present disclosure, appreciate that many changes can be made in the specific embodiments which are disclosed and still obtain a like or similar result without departing from the spirit and scope of the presently disclosed subject matter.

Example 1

Comparison of TLR Ligands as Radio-Mitigators

To examine the role of TLR ligands as radio-mitigators, FSL-1 (TLR2/6 ligand) was first compared with other TLR ligands (FIGS. 1A and 1B). In this experiment, C57BL/6 mice were exposed to 9.2 Gy gamma radiation (total body irradiation, or TBI) using 137-Cesium irradiator and then the mice were treated with TLR ligands via intraperitoneal (IP) injections one day after radiation. The impact of CpG-ODN2395 (CpG, TLR9 agonist), Flagellin FliC (Fla, TLR5 agonist), MPLA (TLR4 agonist) or FSL-1 (Pam2CGDPKHPKSF, TLR2/6 agonist) in comparison to mice treated with physiological water (no treatment, NT) was examined. Survival was monitored over 30 days and clinical scores were recorded. FSL-1 protected 50% of mice from radiation-induced death (FIG. 1A), while other TLR ligands (TLR4, TLR5, TLR9) did not show any protection. Eight independent experiments have been completed, each showing the survival rate of FSL-1-treated mice ranged from 50% to 100% with the mean rate of 80%. The lowest one is presented herein.

The Clinical Score is based on changes to body condition that included body weight, body temperature, physical appearance, grooming, posture, activity/behavior, appetite and hydration. Supplementation with wet feed, subcutaneous fluids, long sipper tubes, were provided as needed. Otherwise, animals were immediately withdrawn and euthanized when body weight loss reached 25%, if animals were unable to remain upright (moribund), showed agonal respiration or suffered convulsions or head tilt/spinning behavior. Compared to other ligands, FSL-1 treated mice clearly showed lower clinical score, indicating radiation-induced injury was reduced by FSL-1 (FIG. 1B).

The radiomitigation activity of TLR2 ligands was delineated (FIGS. 1C and 1D), including FSL-1, by irradiating male C57BL/6 mice and treating (IP injections) with either FSL-1, Pam2CSK4 (Pam2Cys-SKKKK, TLR2/6 ligand), or Pam3CSK4 (Pam3Cys-SKKKK, TLR1/2 ligand) at 24 hours (hr) post TBI. All three TLR2-specific ligands promoted survival, with slight differences evident in animal well-being. However, FSL-1 treatment resulted in lowest clinical scores and protection from weight loss as compared to control mice.

Example 2

Figure 3B:
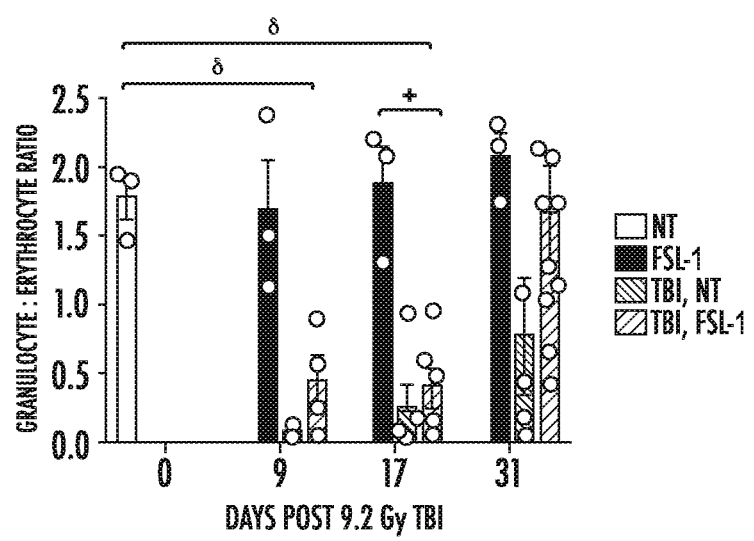
Figure 4A:
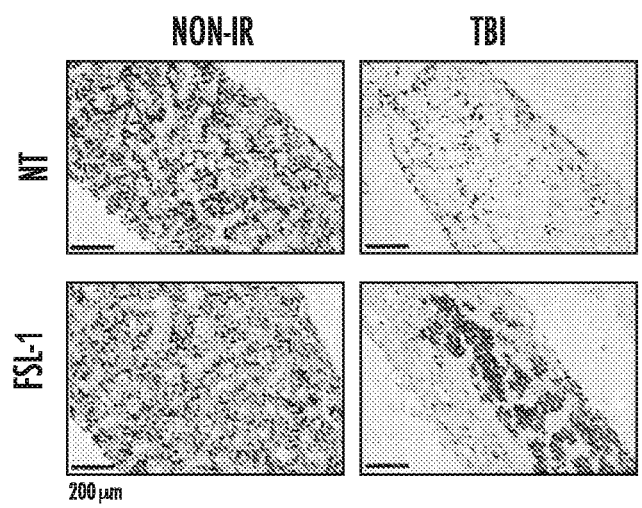
FIGS. 4A and 4B are histological staining images and graphical depictions of data showing that FSL-1 treatment following radiation stimulates proliferative responses in the bone marrow.
Figure 4B:
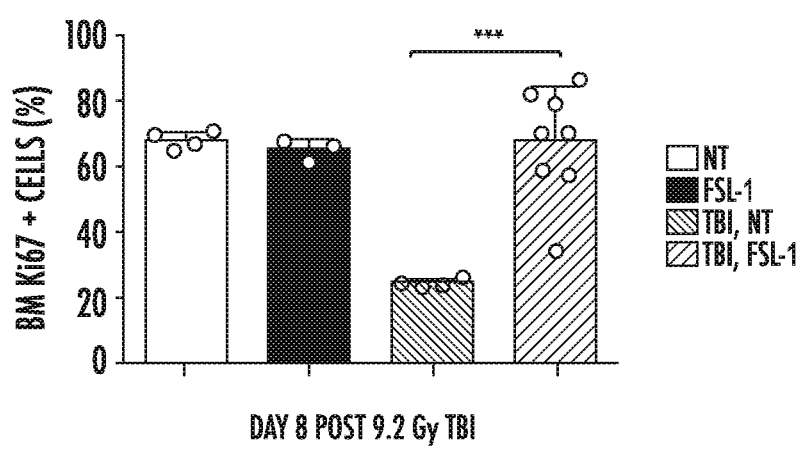

Examination of the Protective Capacity of FSL-1 on Dividing and Regenerating Cells Various hematopoietic sites were analyzed to examine the protective capacity of FSL-1 on dividing and regenerating cells. In animals treated with gamma irradiation followed 24 hr later with FSL-1 (IP, 0.25 mg/kg), the bone marrow showed recovery of cellularity by day 9 that appears to have been fully reconstituted by day 31 (FIGS. 2A through 2C). In contrast, animals exposed to radiation but not receiving FSL-1 showed a delayed recovery profile, with less than 50% of bone marrow cells reconstituted by day 31. Granulocytic cells predominated the recovery of hematopoietic cells as demonstrated in cell smears collected from femurs of FSL-1 treated animals, especially by day 31 (FIGS. 3A through 3B). FSL-1 treatment stimulated proliferative responses as early as day 8 in the bone marrow as displayed by increased Ki67$^+$ staining of bone marrow (FIGS. 4A and 4B).

Example 3

Examination of FSL-1 Effects on Extramedullary Hematopoiesis in the Spleen

Figure 5A:
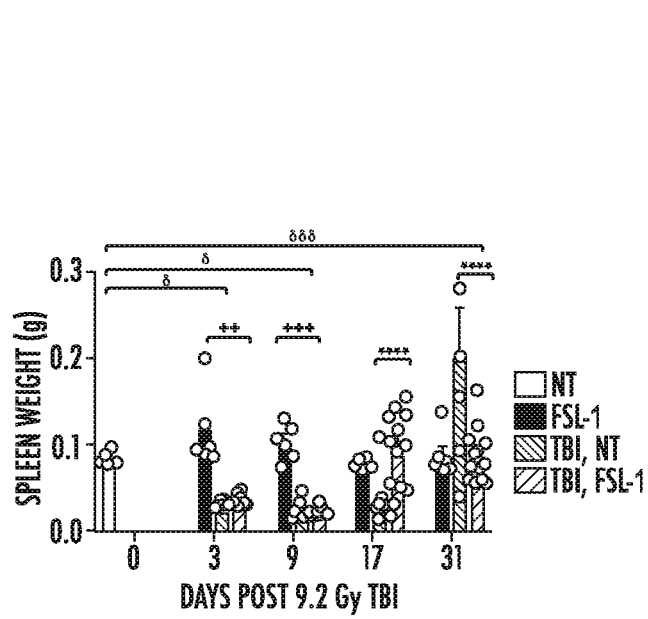
FIGS. 5A through 5C are histological staining images and graphical depictions of data showing that FSL-1 stimulates hematopoiesis in the spleen.
Figure 5B:
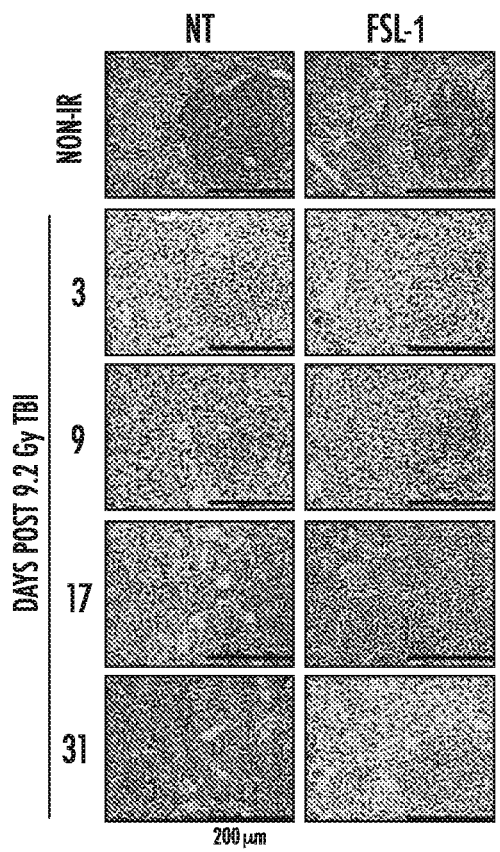
Figure 5C:
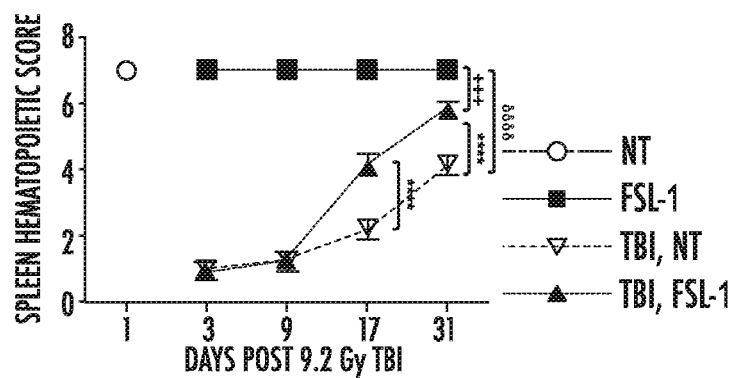

In addition to bone marrow, extramedullary hematopoiesis in the spleen was stimulated by FSL-1 treatment after radiation (FIGS. 5A through 5C). Cellular recovery in the spleen was accelerated by FSL-1 as shown by increased organ weight by day 17 (FIG. 5A) and increased cellularity in spleen from days 9 to 31 (FIGS. 5B and 5C). Hematoxylin and eosin stained spleen tissue sections were analyzed by a certified oncology pathologist who was blinded to the identity of the samples and who provided a quantitative measure of splenic cellularity (FIGS. 5B and 5C).

Example 4

Effects of FSL-1 Treatment on Peripheral Blood Cells

The impact of FSL-1 treatment following radiation on peripheral blood cells was determined (FIGS. 6A through 6F). Blood was collected at various timepoints as a terminal harvesting procedure of mice exposed to radiation followed by a single FSL-1 intraperitoneal (IP) administration. The collected blood was analyzed using Animal Blood Counter to examine clinical chemistry markers: white blood cells (wbc; FIG. 6A), lymphocytes (lym; FIG. 6B), granulocytes (FIG. 6C), monocytes (FIG. 6D), red blood cells (rbc; FIG. 6E) and platelets (plt; FIG. 6F). Although contributing only a small portion to total white blood cell count, increases in monocytes and granulocytes in mice treated with FSL-1 appear to return to baseline, unirradiated levels by day 31 (FIGS. 6C and 6D), while other cell populations (wbc, rbc, plt, lym) show partial recovery. This is in contrast to the case of animals receiving no FSL-1 after radiation that showed delayed and reduced recovery of all blood cell populations in the periphery (FIGS. 6A through 6F).

Example 5

Examination of FSL-1 Activated TLR2 Stimulation on Growth Factors

Figure 7A:
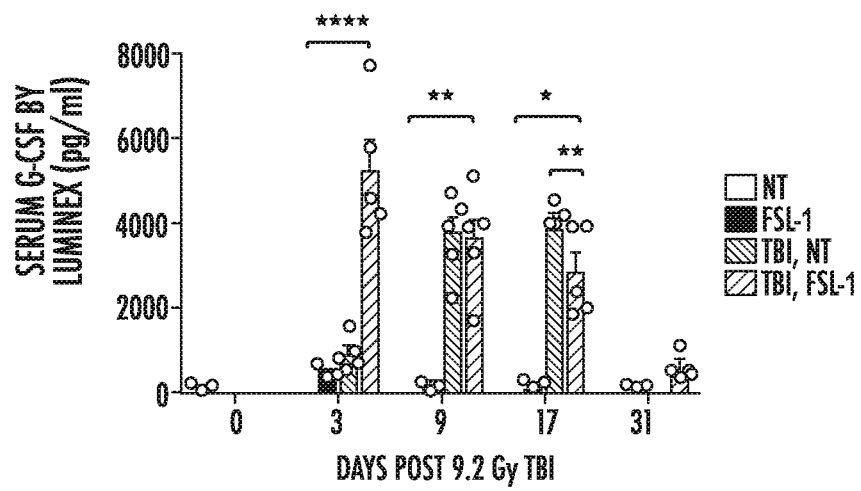
FIGS. 7A and 7B are graphical depictions of data showing that FSL-1 induces G-CSF production.
Figure 7B:
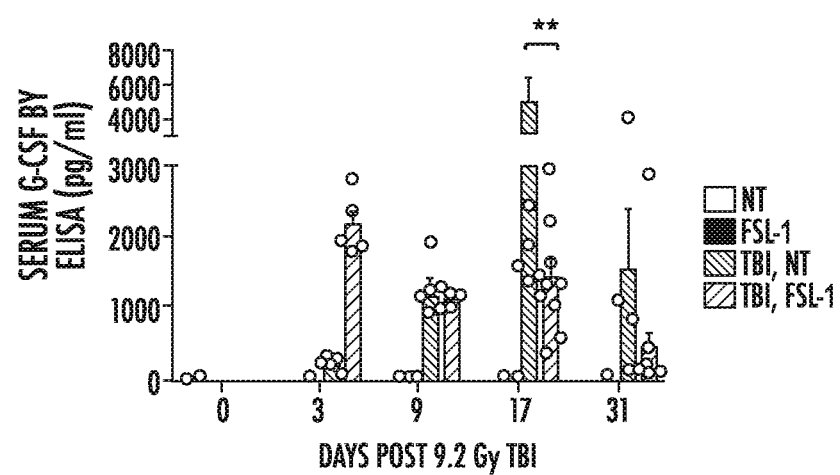

To determine if enhanced H-ARS recovery in FSL-1-treated mice was due to increased cross-talk between TLR2 stimulation and growth factors, serum samples were collected at different time points post TBI and cytokines and chemokines were detected by luminex multiplex analyte and ELISA assays. This study confirmed that activation of TLR2 stimulated G-CSF-directed myeloid cell production. More particularly, the data revealed that G-CSF production kinetics were altered by FSL-1 treatment (FIGS. 7A and 7B). G-CSF was increased in FSL-1-treated, irradiated mice as early as day 3 post TBI, followed by a steady decline observed through day 31 post TBI where levels were similar to that of non-irradiated mice. However, in untreated, irradiated mice, G-CSF was only found at day 9 and peaked at day 17 post-TBI. Thus, FSL-1 induced a significantly faster elevated G-CSF which can trigger hematopoiesis sooner to fight against radiation-induced damage or cytotoxicity.

Example 6

Effects of FSL-1 on Tissue Physiology

Figure 8:
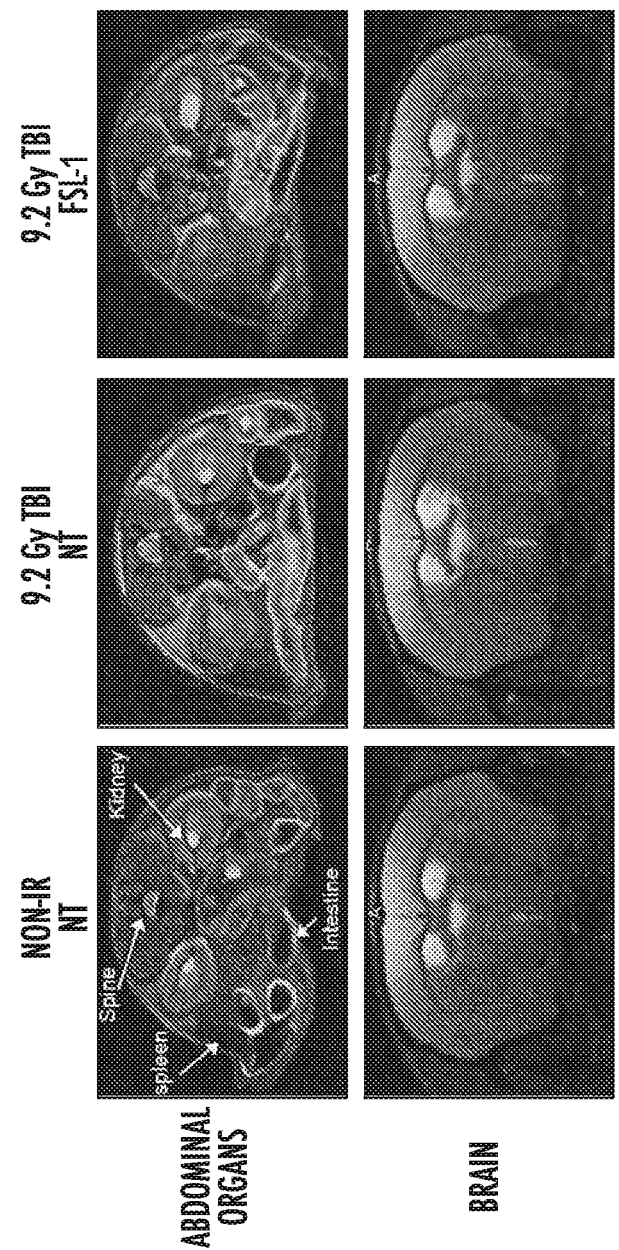
FIG. 8 is a series of Magnetic Resonance Imaging (MRI) images illustrating no long-term defects or tumors in subjects treated with FSL-1.

As for late effects of radiation, mice treated with FSL-1 post TBI that survived for more than 600 days were monitored and showed no symptoms of any diseases (FIG. 8). MRI was used to detect multiple tissues in these survivors, such as brain, gut, kidney or spleen. The results showed no physiologic changes in these tissues, which indicates FSL-1 can not only protect against ARS but can also protect against delayed radiation-induced syndrome and not cause/contribute to tumorigenesis. These results indicate that FSL-1 prolongs survival in mice when administered 24 hours after radiation in an MyD88-dependent fashion in both females and males. FSL-1 is found to accelerate hematopoietic cell recovery in bone marrow, spleen and periphery, and augments systemic levels of hematopoiesis stimulating factors (G-CSF).

Example 7

Figure 9A:
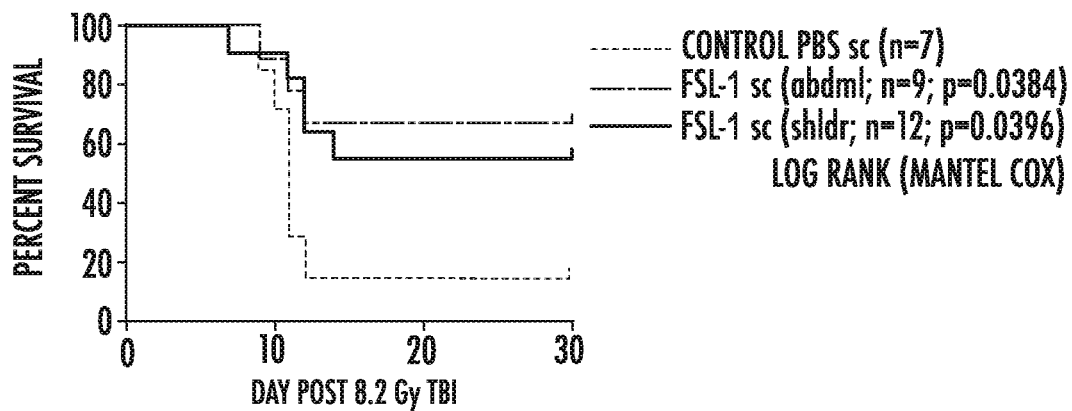
FIGS. 9A through 9C are graphical depictions of data showing subcutaneous administration of FSL-1 mitigates against radiation-induced lethality resulting from different radiation dose exposures.
Figure 9B:
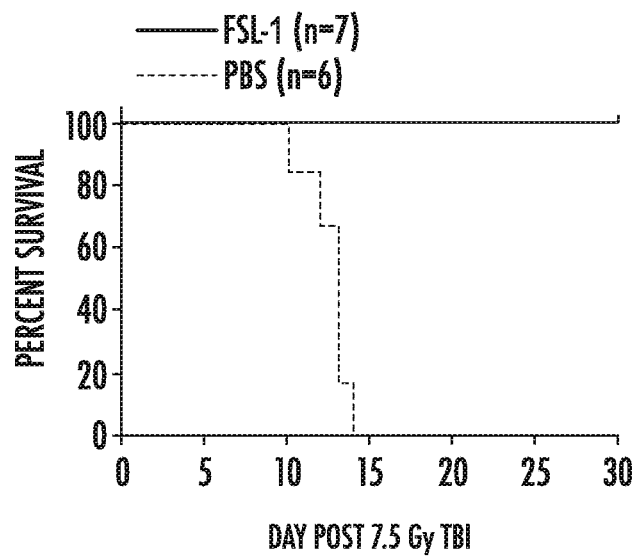
Figure 9C:
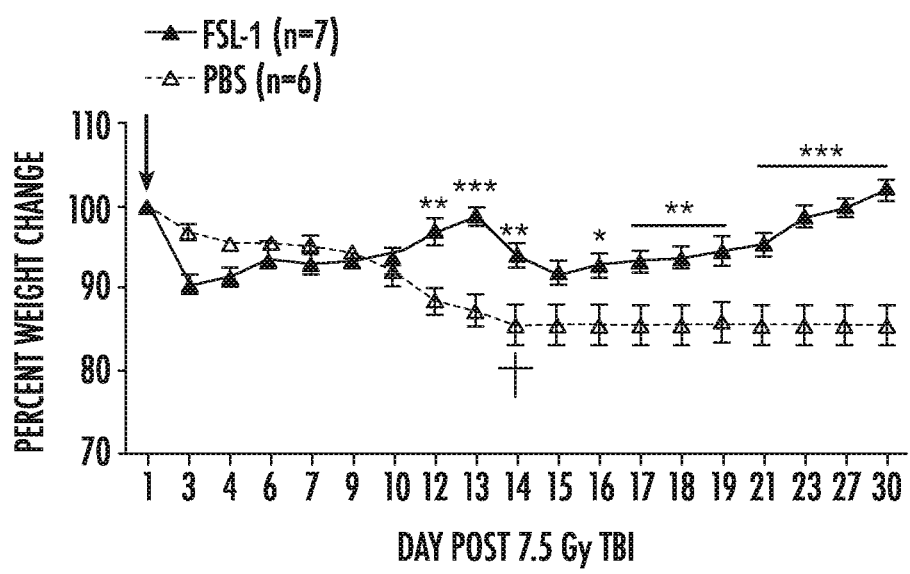

Examination of the Radiomitigation Activity of FSL-1 when Administered Subcutaneously Survival studies were repeated to test the radiomitigation activity of FSL-1 when administered by subcutaneous (SC) route (FIGS. 9A through 9C). Using one of two anatomical locations (shoulder scruff or abdominal flank) to administer FSL-1 under the skin at 24 hr post radiation (8.2Gy), it was found that more than 50% of animals survived for 30 days, while nearly all the PBS administered controls succumbed (FIG. 9A). This survival promotion was consistent with studies where FSL-1 was administered by intraperitoneal injection. Efficacy of SC administration was noted in a second strain of mice (i.e. Balb/c) that were treated with a lower radiation dose. In this case, only animals treated with a single dose of FSL-1 at 24 hr post radiation (7.5Gy TBI) survived and re-gained pre-irradiation weight, while all PBS treated controls succumbed by 14 days (FIGS. 9B and 9C)

Figure 10A:
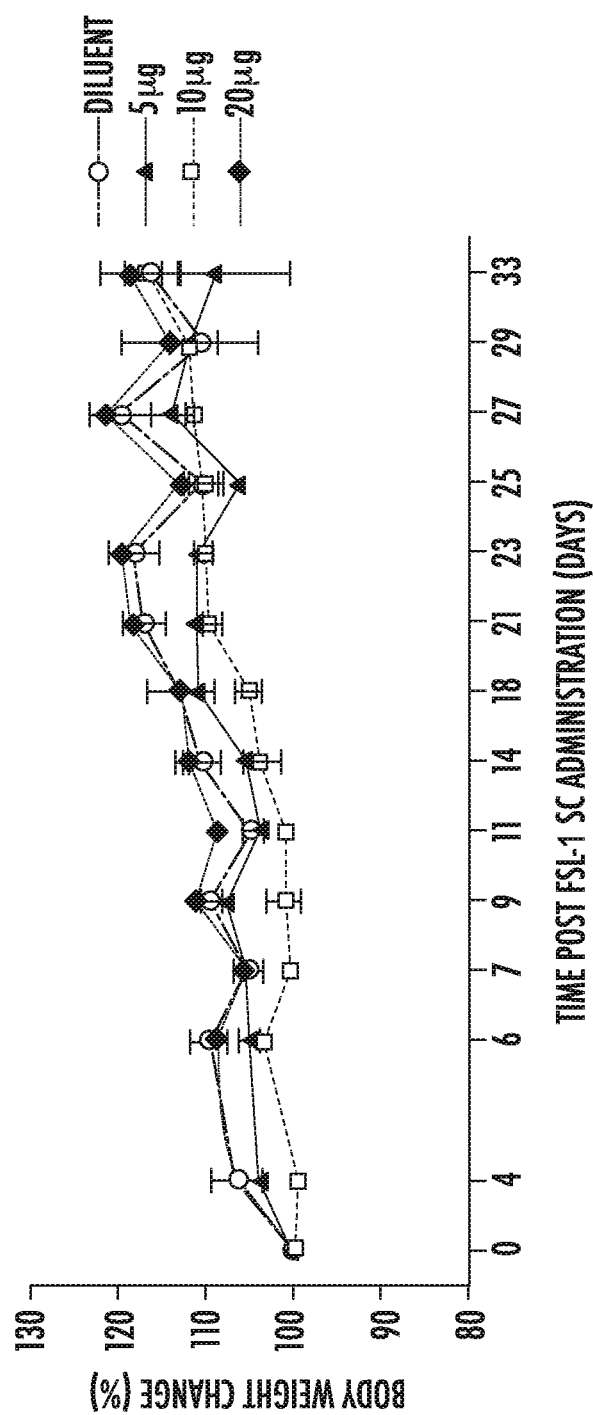
FIGS. 10A and 10B are graphical depictions of data demonstrating that FSL-1 administration by subcutaneous route is safe over a wide dose range.
Figure 10B:
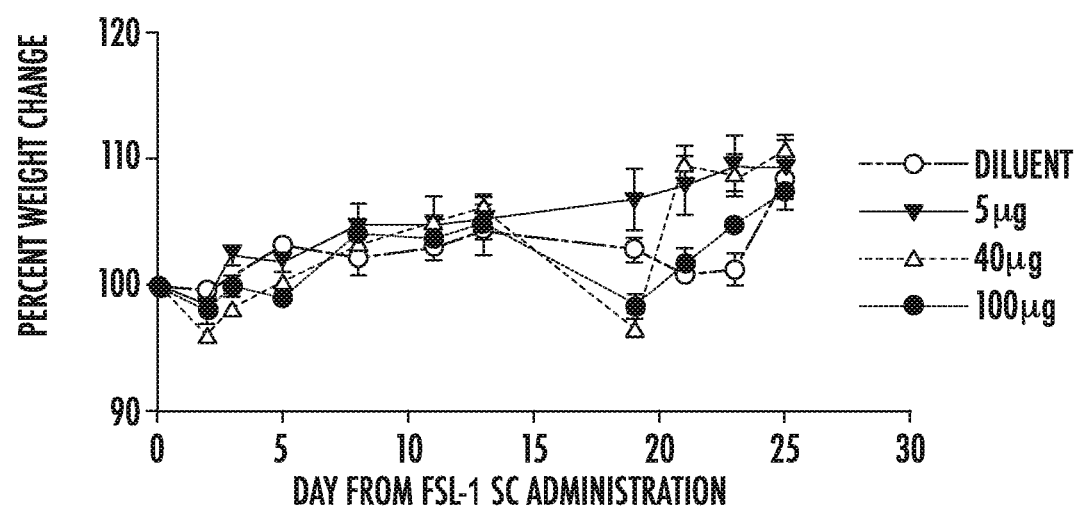

The safety of FSL-1 was further tested by administering increasing doses of FSL-1 using the SC route (abdominal flank), with 5 to 20 µg (FIG. 10A) and then up to 100 µg administered in a single injection (FIG. 10B). Relatively consistent weight or steady weight gain was observed for all doses given, suggesting little to no toxicity. Even upon injection of up to 100 µg FSL-1, there were minimal adverse effects where body temperature dropped no more than 3 degrees (i.e. below 30° C., where 32-33° C. is resting, baseline body temperature of mice) or body weight dropped no more than 15% of initial weight. However, increases in peripheral blood neutrophils were noted 2 to 4 weeks after administration of FSL-1 (30-100 µg). These data indicate that FSL-1 can result in increased neutrophils when injected by the subcutaneous route.

Example 8

FSL-1 Effects on Myeloid Cell Recovery

Figure 11B:
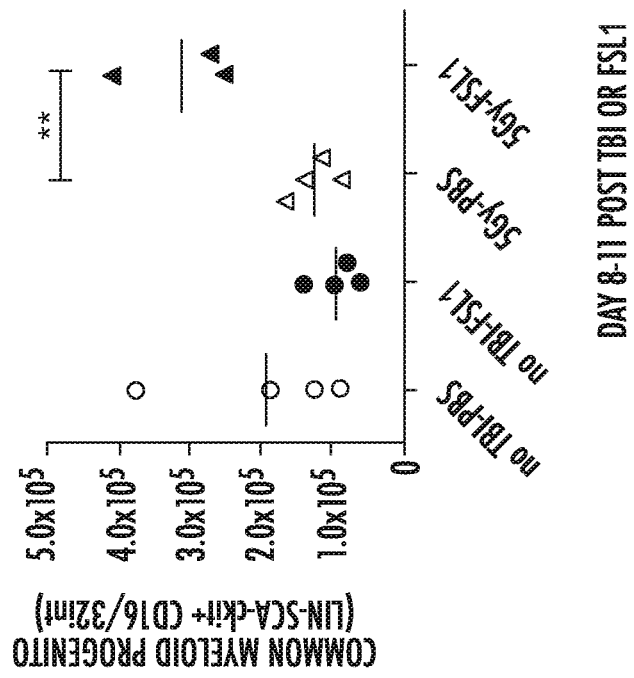
FIGS. 11A and 11B are graphical depictions of data showing that hematopoietic stem and myeloid progenitor cells in bone marrow are increased with FSL-1 treatment post radiation.
Figure 11A:
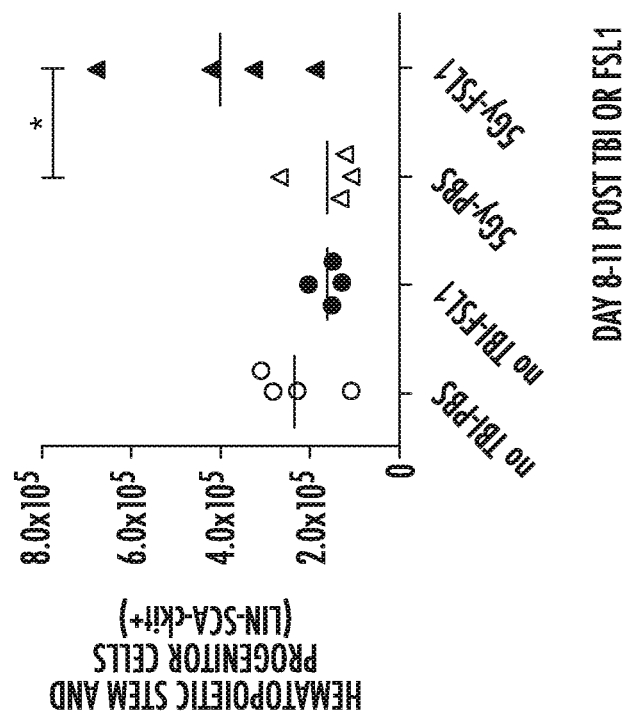
Figure 12:
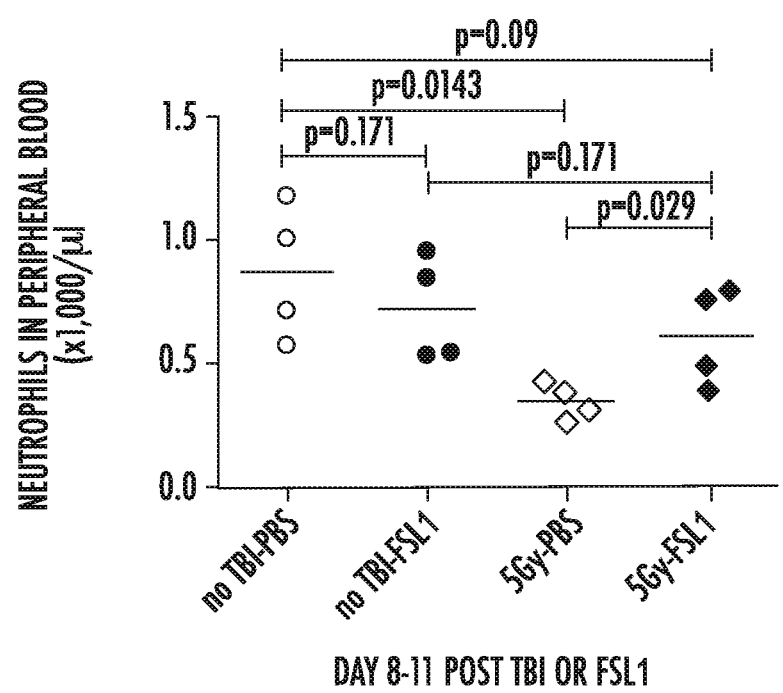
FIG. 12 is a graphical depiction of data showing that neutrophils in peripheral blood are increased to unirradiated levels with FSL-1 treatment post radiation.

To more specifically examine the function of FSL-1 to support myeloid cell recovery after radiation, mice were treated with sub-lethal gamma irradiation (5Gy) followed by FSL-1 injection (0.8 mg/kg, SC) (FIGS. 11A and 11B). With radiation, total bone marrow cells were reduced by more than 50% within one week after exposure. However, we found increases in hematopoietic stem (Lineage$^-$Sca$^+$ c-kit$^-$; FIG. 11A) and common myeloid progenitor (CD16/ 32$^{intermediate}$, lin$^-$Sca$^+$c-kit$^-$; FIG. 11B) cells with FSL-1 treatment after sub-lethal irradiation. These results confirm the activity of FSL-1 in mitigating radiation injury by promoting myeloid cell responses. Furthermore, levels of neutrophils in peripheral blood of irradiated subjects treated with FSL-1 were elevated to levels found in unirradiated animals (FIG. 12).

Example 9

FSL-1 Protection of Gastrointestinal Tissues

Studies were conducted to investigate whether FSL-1 provides protection against radiation-induced injury for other rapidly dividing cell types or tissues by examining pathology of gastrointestinal (GI) tissues. To discern impact of FSL-1 on radiation-induced GI syndrome, the following analyses were conducted: H&E staining of colon samples, western blotting for caspases 3 and 7 in colon tissue extracts, multiplex protein assay of colon explant supernatants, or Ki67$^+$ staining as a proliferation marker in colon samples. All of the resulting data (not shown) showed no difference between FSL-1 treated group versus control group.

Figure 13A:
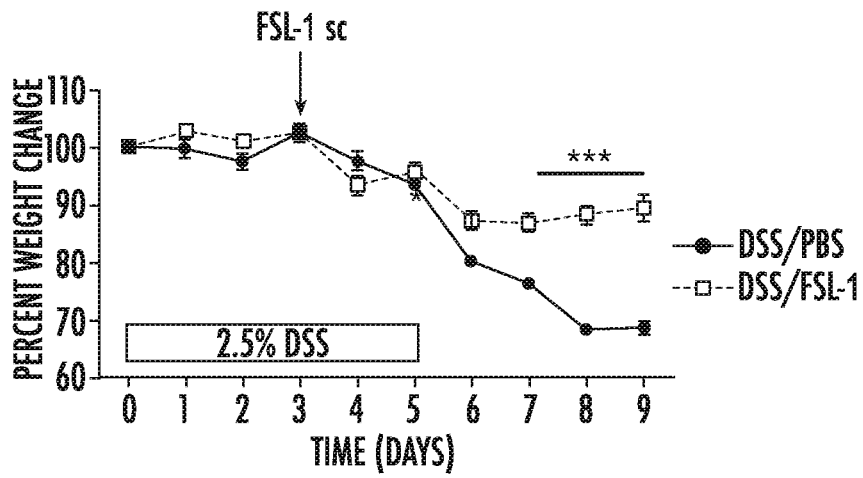
FIGS. 13A through 13D are graphical depictions of data showing that FSL-1 protects against inflammation-induced gastrointestinal epithelia injury and lethality.
Figure 13B:
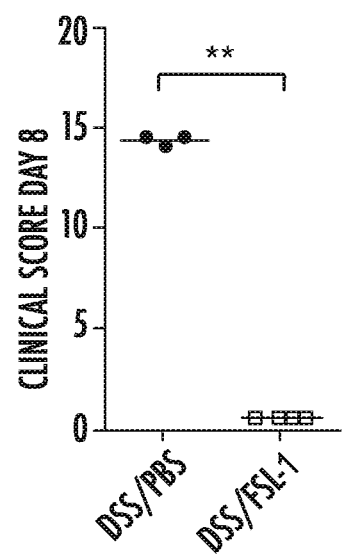
Figure 13C:
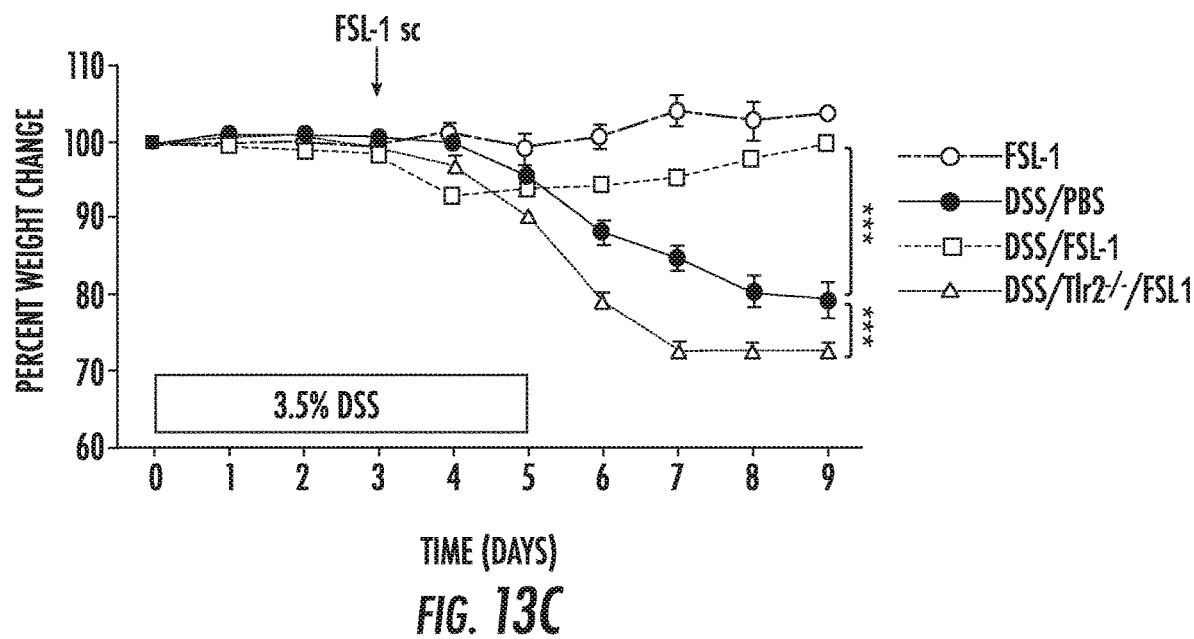
Figure 13D:
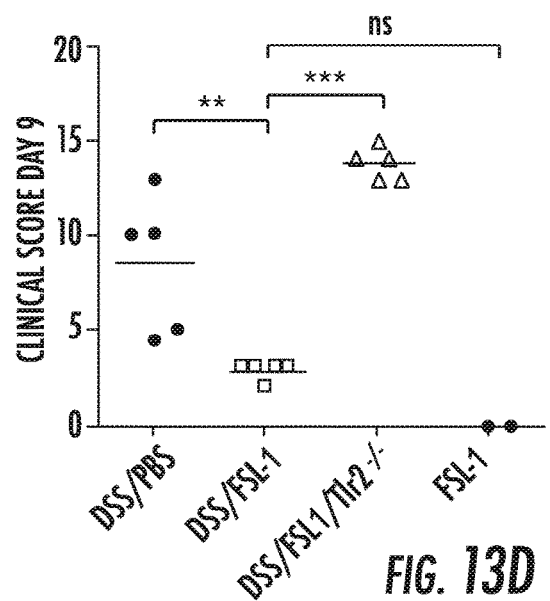

As an alternative approach to examining FSL-1 activity in recovery in the gastrointestinal system, an acute colitis model in mice using dextran sodium sulfate (DSS) treatment was used (FIGS. 13A through 13D). In this model, mice are given water ad libitum that is spiked with 2-4% DSS, a detergent that causes GI epithelial injury and therefore increases GI barrier permeability. After 5 days on DSS supplemented water, mice were given regular water, while disease/clinical symptoms (i.e. bloody stool, diarrhea, weight loss) increase if epithelial cells do not recover from the inflammatory insult. When FSL-1 was tested in the DSS model (given on day 3), it was found that FSL-1 treated animals displayed minimal weight loss with significantly fewer clinical symptoms (FIG. 13A). On the other hand, PBS-treated controls did not recover from the DSS treatment and displayed high clinical scores, including bloody stool, diarrhea, dehydration, hunched postures and declining body condition (FIG. 13B). In additional studies, this GI protective phenomena was replicated and specificity to TLR2 activation mediated by FSL-1 was confirmed. Unlike wild type animals treated with FSL-1, Tlr2-deficient animals were unable to recover from the GI inflammatory insults of DSS exposure and developed high clinical scores (FIGS. 13C and 13D).

Example 10

Figure 14A:
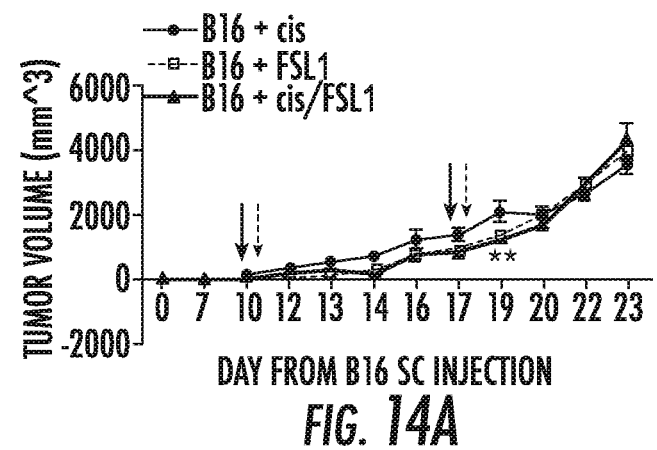
FIGS. 14A and 14B are graphical depictions of data showing that FSL-1 administered with chemotherapy supports tumor growth control and management of adverse effects.
Figure 14B:
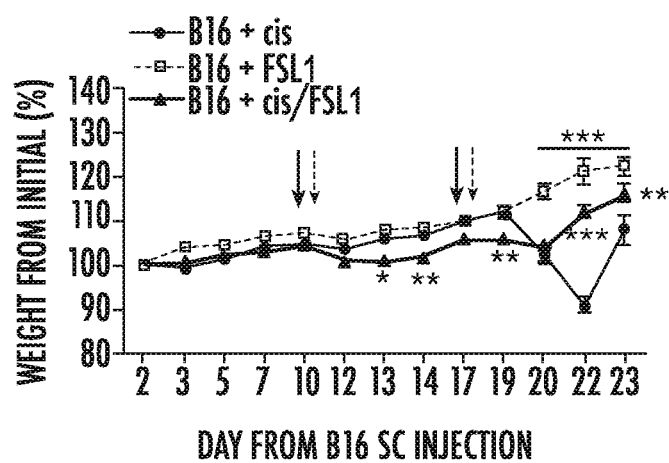

Examination of the Anti-Cancer Effects of FSL-1 in Conjunction with Chemotherapy The impact of combining FSL-1 treatment with chemotherapy as a therapeutic against cancer was also tested. In this study, B16 melanoma tumor cells (50,000) in matrigel matrix were implanted into the flank (SC) of wild type animals and were allowed to grow 10 days to palpation (~3-5 mm in diameter). Mice were then treated with chemotherapy agent cisplatin (intravenous IV, 100 µg/mouse) with and without FSL-1 (SC, 40 µg/mouse). Changes in tumor volume (ellipsoidal volume calculation of ½ width*width*length, mm$^3$) were monitored along with changes in body weight and condition. Tumors in mice treated with combined regimen were significantly smaller, showing a greater regulation of tumor growth using the combined FSL-1 with chemotherapy (FIG. 14A). Additionally, tumors in animals treated with FSL-1 alone were also restricted in growth, with only 1 animal reaching humane endpoint of 2 cm diameter tumor size by day 20 while two animals treated only with cisplatin reaching the 2 cm tumor diameter endpoint by day 19. Importantly, animals treated with FSL-1 in combination with cisplatin or FSL-1 alone maintained weight for nearly 2 weeks following treatment, while animals receiving only cisplatin dramatically lost weight after day 19 and showed reduced body condition, indicating the combined regimen was beneficial for managing adverse effects (FIG. 14B). These results suggest that addition of FSL-1 is superior to a standard chemotherapy alone in the control of an aggressive melanoma that is resistant to most treatment and in mitigating secondary adverse effects.

Example 11

Conclusions and Analysis

In summary, the instant disclosure includes data demonstrating for the first time that FSL-1: (1) mitigates the side effects of radiation, (2) increases G-CSF and hematopoietic cell recovery, (3) increases blood neutrophils, (4) can be administered through an intraperitoneal or subcutaneous route, (5) increases hematopoietic stem cells and common myeloid progenitors, (6) mitigates gastrointestinal colitis and (7) causes a reduction in tumor growth in a tumor model that is difficult to treat.

REFERENCES

All references listed herein including but not limited to all patents, patent applications and publications thereof, scientific journal articles, and database entries are incorporated herein by reference in their entireties to the extent that they supplement, explain, provide a background for, or teach methodology, techniques, and/or compositions employed herein.

Shibata, K I. et al., 2000, The N-terminal lipopeptide of a 44-kDa membrane-bound lipoprotein of Mycoplasma salivarium is responsible for the expression of intercellular adhesion molecule-1 on the cell surface of normal human gingival fibroblasts. *J. Immunol.* 165:6538-6544.

Okusawa T. et al., 2004, Relationship between Structures and Biological Activities of Mycoplasmal Diacylated Lipopeptides and Their Recognition by Toll-Like Receptors 2 and 6. *Infect Immun.* 72(3): 1657-1665.

Takeuchi O. et al., 2001. Discrimination of bacterial lipoproteins by Toll-like receptor 6. *Int Immunol.* 13(7):933-40.

Kurkjian C J et al., The Toll-Like Receptor 2/6 Agonist, FSL-1 Lipopeptide, Therapeutically Mitigates Acute Radiation Syndrome. *Sci Rep.* 2017 Dec. 11;7(1):17355.

Shakhov et al. Shakhov, A. N. et al. Prevention and mitigation of acute radiation syndrome in mice by synthetic lipopeptide agonists of Toll-like receptor 2 (TLR2). *PLoS One* 7, e33044 (2012).

Singh V K et al. CBLB613: a TLR 2/6 agonist, natural lipopeptide of Mycoplasma arginini, as a novel radiation countermeasure. *Radiat Res.* 2012 May;177(5):628-42. Epub 2011 December 16.

Gao, F. et al. A critical role of toll-like receptor 2 (TLR2) and its' in vivo ligands in radio-resistance. *Sci. Rep.* 5, 13004 (2015).

Zhang, C. et al. Radioprotection of bone marrow hematopoiesis by CpG-oligodeoxynucleotides administered to mice after total-body irradiation. *J. Radiat. Res.* 52, 828-833 (2011).

Zhang, C. et al. CpG-Oligodeoxynucleotide Treatment Protects against Ionizing Radiation-Induced Intestine Injury. *PLoS One* 8, (2013).

Vijay-Kumar, M. et al. Flagellin treatment protects against chemicals, bacteria, viruses, and radiation. *J. Immunol.* 180, 8280-8285 (2008).

Liu, C. et al. A critical role of toll-like receptor 4 (TLR4) and its' in vivo ligands in basal radio-resistance. *Cell Death Dis.* 4, e649 (2013).

Avalos, B. R., Lazaryan, A. & Copelan, E. A. Can G-CSF cause leukemia in hematopoietic stem cell donors? *Biol. Blood Marrow Transplant.* 17, 1739-1746 (2011).

Smith, R. E., Bryant, J., DeCillis, A. & Anderson, S. Acute myeloid leukemia and myelodysplastic syndrome after doxorubicin-cyclophosphamide adjuvant therapy for operable breast cancer: the National Surgical Adjuvant Breast and Bowel Project Experience. *J. Clin. Oncol.* 21, 1195-1204 (2003).

Khoury, H. et al. Adverse side-effects associated with G-CSF in patients with chronic myeloid leukemia undergoing allogeneic peripheral blood stem cell transplantation. *Bone Marrow Transplant.* 25, 1197-1201 (2000).

Freedman, M. H. et al. Myelodysplasia syndrome and acute myeloid leukemia in patients with congenital neutropenia receiving G-CSF therapy. *Blood* 96,429-436 (2000).

van Os R, Robinson S, Sheridan T, Mislow J M, Dawes D, Mauch P M. Granulocyte colony-stimulating factor enhances bone marrow stem cell damage caused by repeated administration of cytotoxic agents. *Blood.* 1998 September 15;92(6):1950-6. PMID: 9731052.

Allen I C et al. The NLRP3 inflammasome functions as a negative regulator of tumorigenesis during colitis-associated cancer. *J Exp Med.* 2010 May 10;207(5):1045-56.

Wilson J E et al. Inflammasome-independent role of AIM2 in suppressing colon tumorigenesis via DNA-PK and Akt. *Nat Med.* 2015 August;21(8):906-13.

Johnson S M et al. Mitigation of hematologic radiation toxicity in mice through pharmacological quiescence induced by CDK4/6 inhibition. *J Clin Invest.* 2010 July;120 (7):2528-36.

Gude R P et al. Effects of niosomal cisplatin and combination of the same with theophylline and with activated macrophages in murine B16F10 melanoma model. *Cancer Biother Radiopharm.* 2002 April; 17(2): 183-92.

FDA White Paper (http://www.fda.gov/cder/guidance/index.htm): Guidance for Industry: Estimating the Maximum Safe Starting Dose in Initial Clinical Trials for Therapeutics in Adult Healthy Volunteers. July 2005, Pharmacology and Toxicology Nair A B and S. Jacob. A simple practice guide for dose conversion between animals and human. *J Basic Clin Pharm.* March 2016-May 2016; 7(2): 27-31.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of mitigating and/or preventing side effects from chemotherapy in a subject, the method comprising
   administering to the subject a therapeutically effective amount of a fibroblast-stimulating lipopeptide 1 (FSL-1),
   wherein side effects from chemotherapy are substantially mitigated and/or prevented in the subject.

2. The method of claim 1, wherein the FSL-1 is administered orally, intraperitoneally or subcutaneously.

3. The method of claim 1, wherein administration of FSL-1 attenuates hematopoietic and/or gastrointestinal syndrome caused by the chemotherapy.

4. The method of claim 1, wherein administration of FSL-1 causes a stimulation or an increase in the subject of one or more of: hematopoietic cell recovery, production of granulocytic cells, proliferative responses in bone marrow, hematopoiesis in a spleen, hematopoietic cell recovery causing an increase in peripheral blood cell populations, granulocyte colony-stimulating factor (G-CSF) production, hematopoietic stem cell production and myeloid progenitor cell production in bone marrow, and neutrophil production in peripheral blood.

5. The method of claim 1, wherein administration of FSL-1 protects against inflammation-induced gastrointestinal epithelia injury in the subject.

* * * * *